United States Patent [19]

Duggan

[11] Patent Number: 4,692,147
[45] Date of Patent: Sep. 8, 1987

[54] DRUG ADMINISTRATION DEVICE

[75] Inventor: Stephen R. Duggan, Rosemount, Minn.

[73] Assignee: Medtronic, Inc., Minneapolis, Minn.

[21] Appl. No.: 757,092

[22] Filed: Jul. 19, 1985

Related U.S. Application Data

[63] Continuation of Ser. No. 591,739, Mar. 21, 1984, abandoned, which is a continuation of Ser. No. 348,384, Feb. 12, 1982, abandoned, which is a continuation of Ser. No. 136,510, Apr. 2, 1980, abandoned.

[51] Int. Cl.4 ............................................. A61M 31/00
[52] U.S. Cl. ............................. 604/93; 128/DIG. 12; 604/891
[58] Field of Search ....................... 604/31, 50, 65, 66, 604/67, 70, 93, 890, 164, 891; 128/DIG. 12, DIG. 13, 419 PG, 419 PT

[56] References Cited

U.S. PATENT DOCUMENTS

| | | | |
|---|---|---|---|
| 3,527,220 | 9/1970 | Summers | 604/153 |
| 3,547,127 | 12/1971 | Anderson | 128/419 PG |
| 3,731,679 | 5/1973 | Wilhelmson et al. | 128/DIG. 13 |
| 3,951,147 | 4/1976 | Tucker et al. | 604/891 |
| 3,990,444 | 11/1976 | Vial | 128/DIG. 12 |
| 3,995,623 | 12/1976 | Blake et al. | 128/642 |
| 4,013,074 | 3/1977 | Siposs | 604/891 |
| 4,037,598 | 7/1977 | Georgi | 128/DIG. 13 |
| 4,077,405 | 3/1978 | Haerten et al. | 128/DIG. 12 |
| 4,137,913 | 2/1979 | Georgi | 604/67 |
| 4,146,029 | 3/1979 | Ellinwood, Jr. | 604/891 |
| 4,210,138 | 7/1980 | Jess et al. | 128/DIG. 12 |
| 4,245,641 | 1/1981 | Mann et al. | 128/419 PG |
| 4,265,241 | 5/1981 | Portner et al. | 128/DIG. 12 |
| 4,529,401 | 7/1985 | Leslie et al. | 604/67 |

Primary Examiner—William E. Kamm
Attorney, Agent, or Firm—John L. Rooney; Joseph F. Breimayer; Robert C. Beck

[57] ABSTRACT

An implantable drug administration device can be noninvasively programmed to change both the dosage amount and the dosage interval. Verification of received dosage and interval commands is being achieved by means of an audio transducer which is attached to the device case. Application of a magnet or a programmer to the device inhibits drug delivery.

11 Claims, 24 Drawing Figures

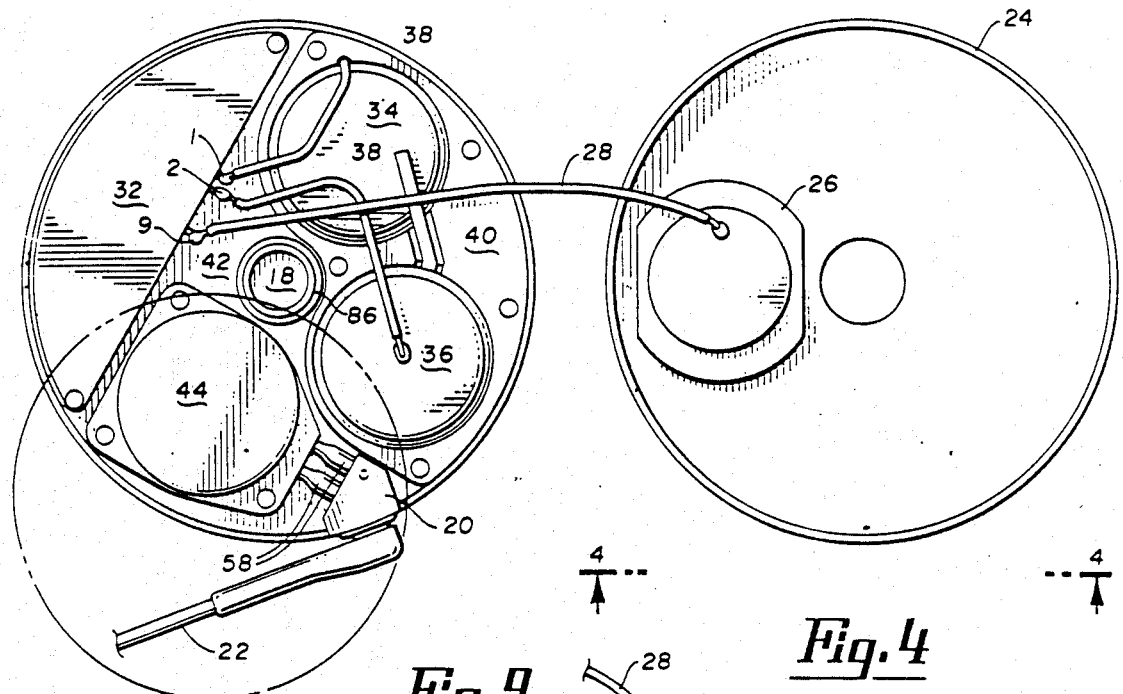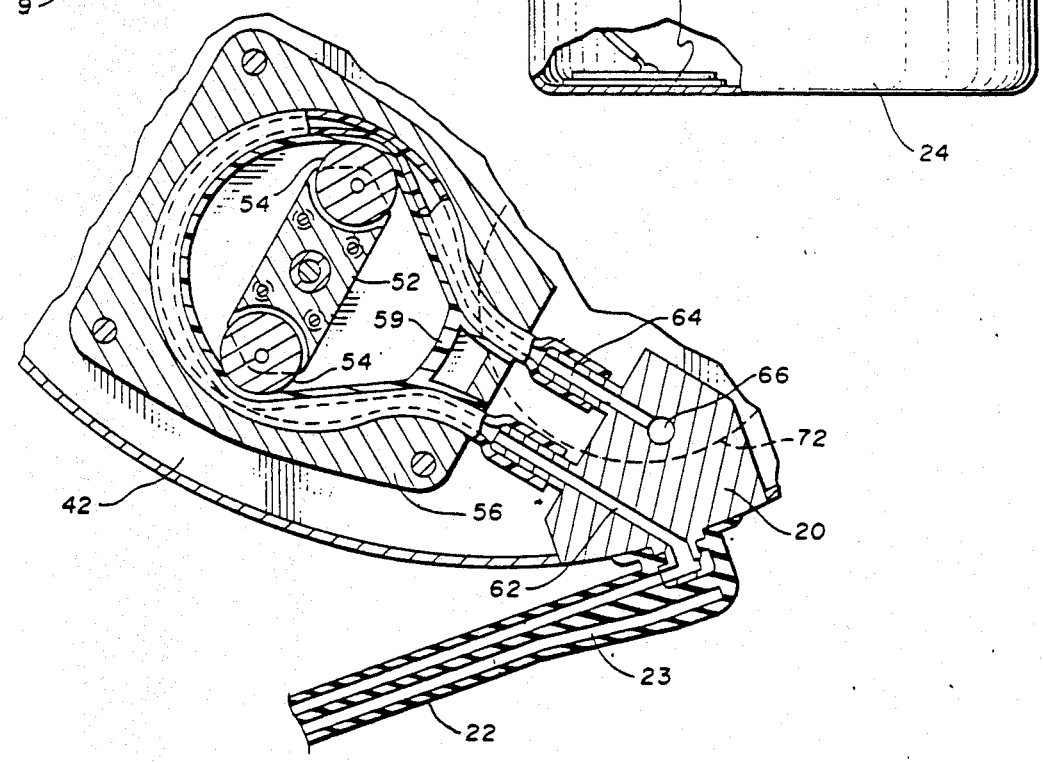

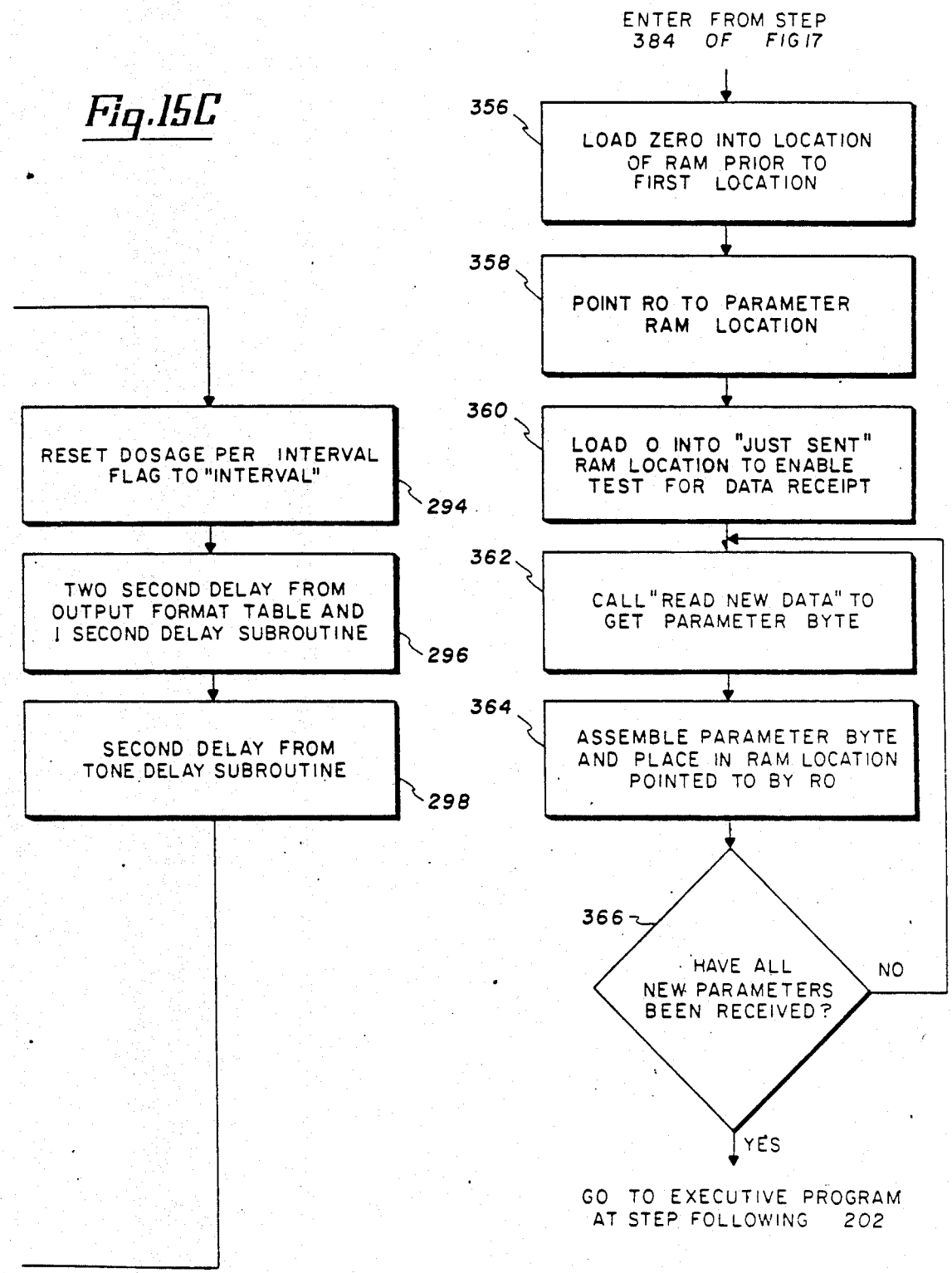

DRUG ADMINISTRATION DEVICE

This is a continuation of co-pending application Ser. No. 591,739 filed on Mar. 21, 1984, which is a continuation of Ser. No. 348,384, filed on Feb. 21, 1982, which is a continuation of Ser. No. 136,510 filed on Apr. 2, 1980 all now abandoned.

FIELD OF THE INVENTION

This invention relates to apparatus for internally implanted electronic devices adapted to be operated to deliver a fluid medicine to a desired location within a human body.

DESCRIPTION OF THE PRIOR ART

A number of approaches have been followed in the prior art for the dispensing of medical substances in the body.

In U.S. Pat. No. 3,527,220, an implantable drug administrator is shown which operates with a refillable bladder reservoir and a roller pump which is driven by a magnet located outside the body.

In U.S. Pat. No. 3,951,147, a reservoir is formed from a bellows enclosed within a housing. The contents of the reservoir are pressurized by a fluorocarbon fluid located in the space between the housing and bellows. The unit continuously dispenses the liquid to the body site through a capillary tube.

In U.S. Pat. No. 4,146,029, a dispenser is shown which dispenses drugs in a predetermined manner which may be modified somewhat by means external to the body. A piston and bellows pumping device is used to dispense the drug.

A problem with such prior art, implantable drug administration devices is that there was no way to provide a simple external means to select the dosage amounts and intervals from a wide range of possible doses and intervals, and verify that a desired change had been made. Still another problem is the lack of provision in the prior art for a simple means to inhibit operation of the device.

SUMMARY OF THE DISCLOSURE

In accordance with one aspect of this invention, there is provided a drug administration device for providing a measured dosage of a medical liquid to a location within the body comprising a pump for metering a measured amount of drug from said device in response to a pulse, a triggerable circuit for generating a pulse and a digital computer operable at predetermined intervals to trigger said circuit to generate a plurality of pulses to deliver measured drug dosages at selected intervals.

The device is programmed as to dosage and interval by an external programmer. A "special" external programmer can reprogram an implanted device to alter its "personality" ie. the duration of the stepper motor drive pulses, the delay time between pulses and the number of pulses to be dispensed for a dosage command can all be altered.

BRIEF DESCRIPTION OF THE DRAWINGS

The advantages of the present invention will become more apparent by referring to the following detailed description and accompanying drawings, in which:

FIG. 3 is a plan view of the drug administration device of FIG. 2, but with the covering shield removed and turned over along side;

FIG. 4 is a view of covering shield taken along line 4—4 of FIG. 3;

FIG. 9 is a section of pump/meter taken along line 9—9 of FIG. 1, and a detail of FIG. 3 taken at 9 thereof and shown in enlarged scale;

FIG. 18 is a flow chart of the Accept New Parameters Subroutine; and

DESCRIPTION OF THE PREFERRED EMBODIMENT

Figure 1:
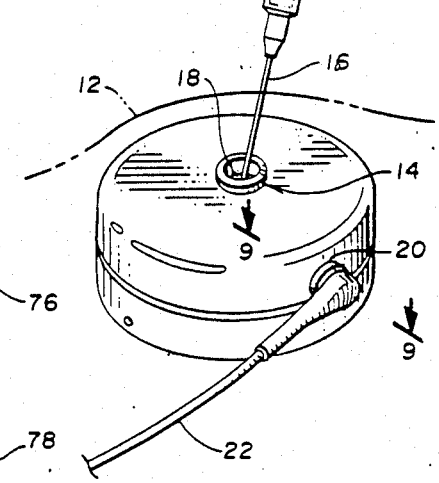
FIG. 1 is a pictorial view of the drug administration device implanted beneath skin (shown in phantom) with the reservoir thereof being filled by means of a hypodermic syringe.

Referring now to FIG. 1, the drug administration device 10 is shown implanted below a layer of skin 12, shown in phantom outline only. The drug administration device has a port 14 into which a hypodermic needle 16 can be inserted through the skin 12 to insert a quantity of a liquid drug, such as heparin, morphine, or some other drug, through a septum 18 into a drug reservoir A located within the drug administration device 10. The liquid drug is delivered from the drug administration device 10 through a catheter port 20 to which a catheter 22 is attached. The catheter 22 is positioned to deliver the medication to a particular point in the body. The catheter has a separate lumen 23 shown in FIG. 9 to permit it to be positioned at the time of implant, using a suitable stylet.

Figure 11A:
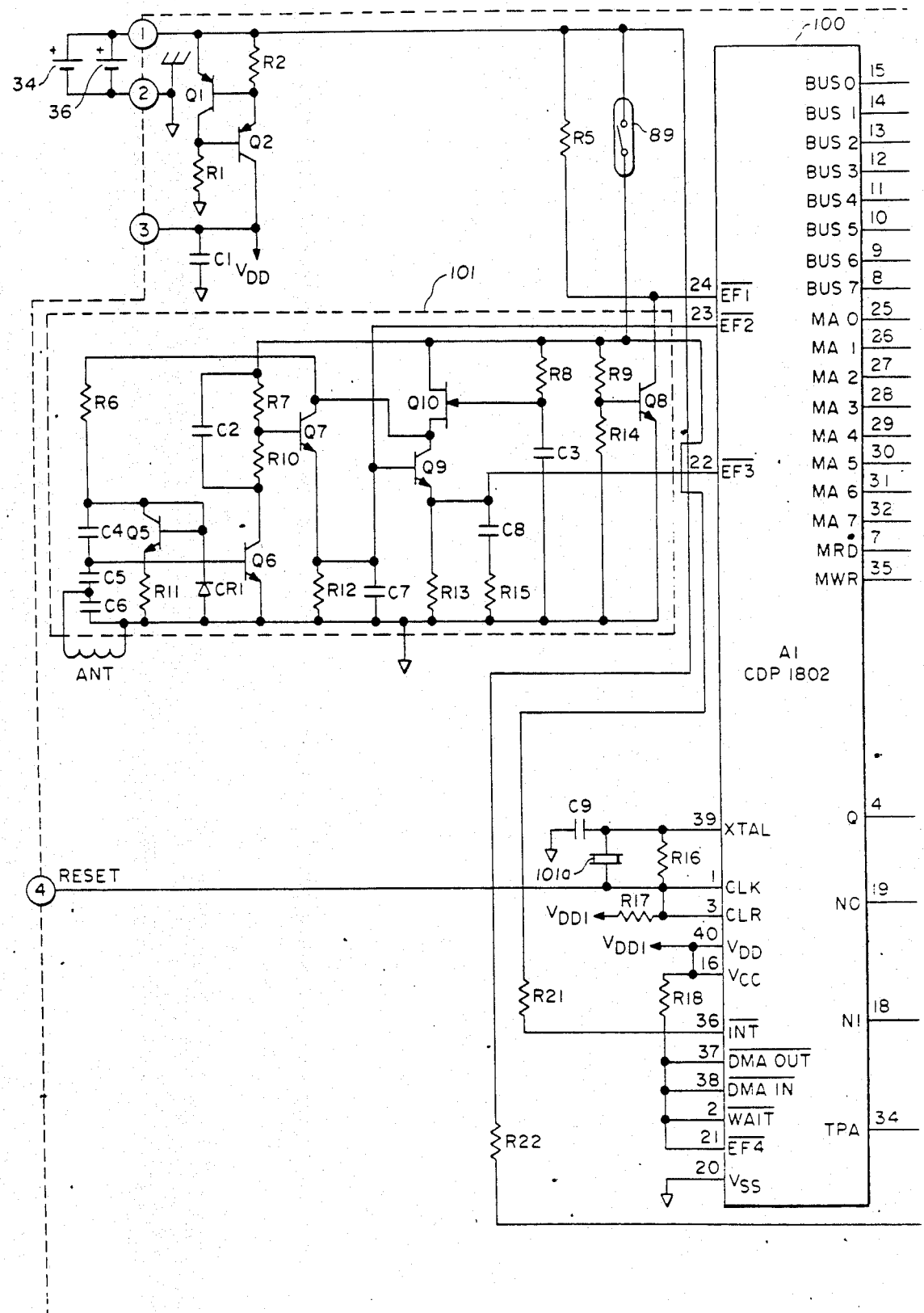
FIGS. 11A and 11B are a datailed schematic diagram of the electronics module of the drug administration device.
Figure 11B:
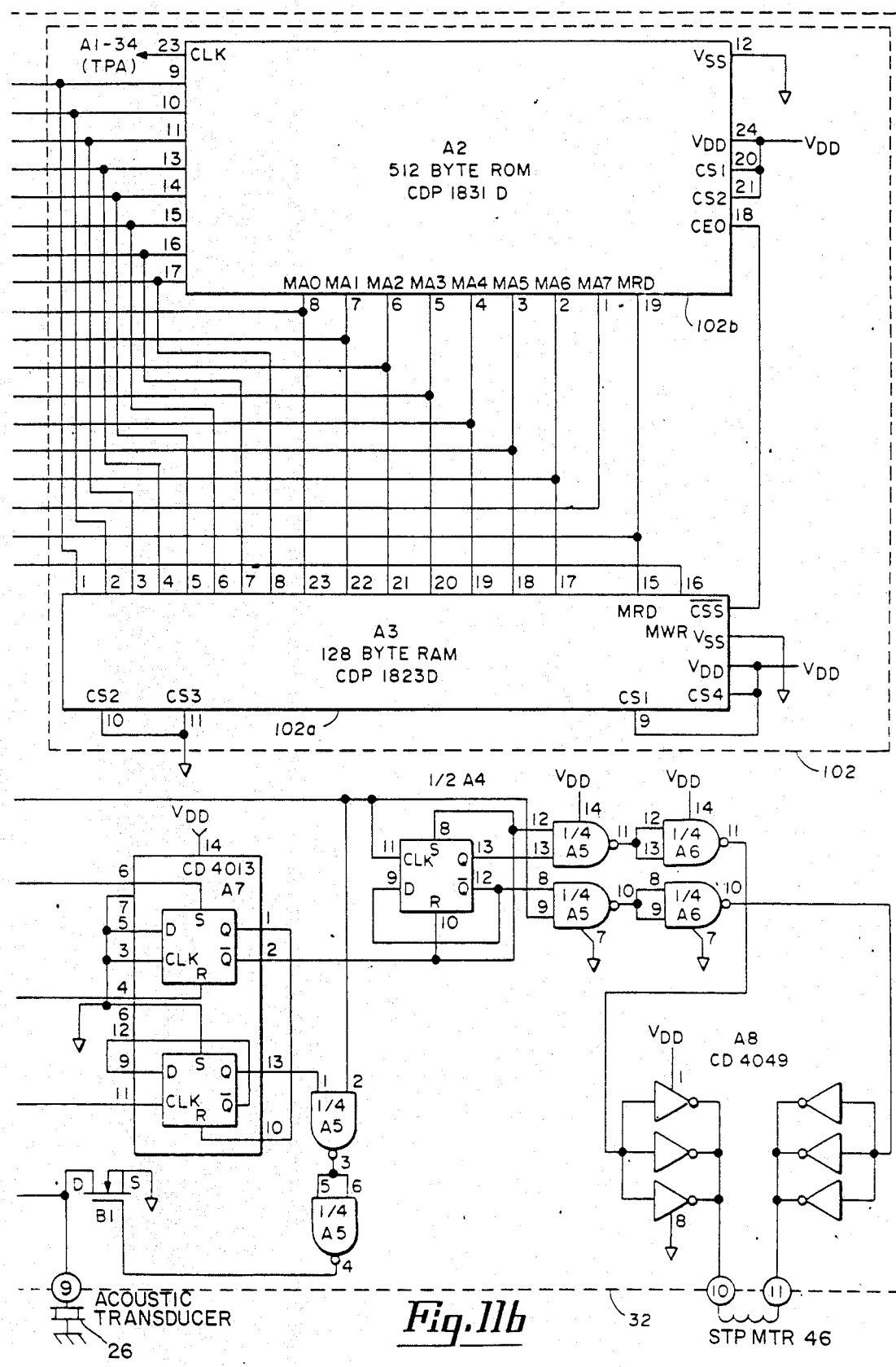

FIG. 3 shows the drug administration device with the covering shield 24 removed. The shield is formed from titanium or some similar appropriate non-magnetic material, as are the other parts of the device which are exposed to body tissue and fluids in the implanted unit. A resonator, annunciator or transducer 26 is bonded to the inner surface of shield 24, as is shown in FIGS. 3 and 4. Transducer 26 is suitable for producing an audio output audible outside the body when excited by an electrical signal in the audio range. The shield 24 is excited by transducer 26, to facilitate transmission of the audio energy from the body. A suitable transducer 26 can be purchased from Kyocero International. The transducer is driven by a conductor 28 connected to an output terminal 9 of an electronic module 32 which has a detailed electrical schematic as shown in FIGS. 11A and 11B.

The circuit module 32 is driven by suitable batteries 34 and 36, which are connected to the battery input terminals 1 and 2 of the electronic module 32 by suitable conductors 38. The batteries are restrained from movement within the device by a non-inductive spacer cup 40 which is attached to the frame 42 of the device.

Figure 10:
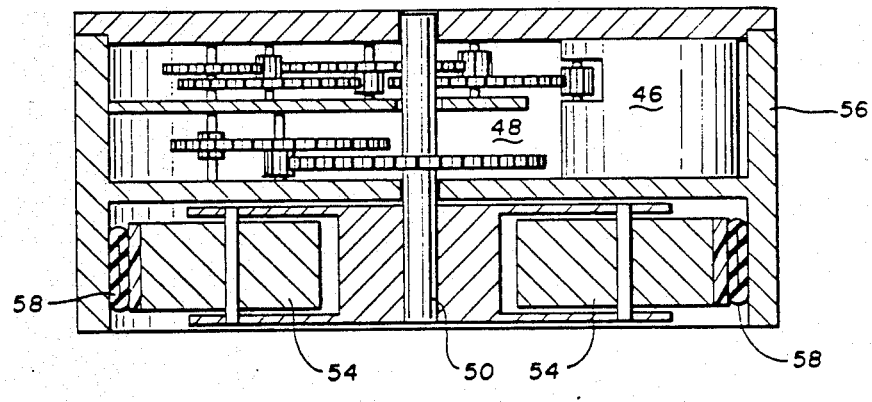
FIG. 10 is a section of the pump taken along line 10—10 of FIG. 9.

Also attached to frame 42, is the metering pump 44. Pump 44, which is shown in more detail in FIGS. 9 and 10, is a roller pump. In FIG. 10, it can be seen that a motor 46 drives a gear train 48, which in turn drives a shaft 50 which is connected to an arm 52. Motor 42 is a two pole subminiature stepping motor of the type used in digital watches having analalog time indicating means. Such motors are manufactured by Seiko Corporation. The winding of Motor 42 is driven by electrical pulses from pins 10 and 11 of electronics module 32, which step the motor through a fixed arc for each pulse.

Rollers 54 are each mounted for rotation about their axes at both ends of arm 52, which is rotatable through 360°. As shaft 50 is rotated, arm 52 and rollers 54 are rotated about the axis of shaft 50. The arm is located within a housing 56 and a flexible tube 58 lines the interior wall of housing 56 as shown in FIG. 9. A shim 59 is interposed between rollers 54 and tubing 58 to aid in balancing the forces applied to shaft 50 as rollers 54 traverse a complete revolution of shaft 50. As shaft 50 rotates, the wheels 54 roll along shim 59 and compress tubing 58 against the inner wall of housing 56.

Figure 6:
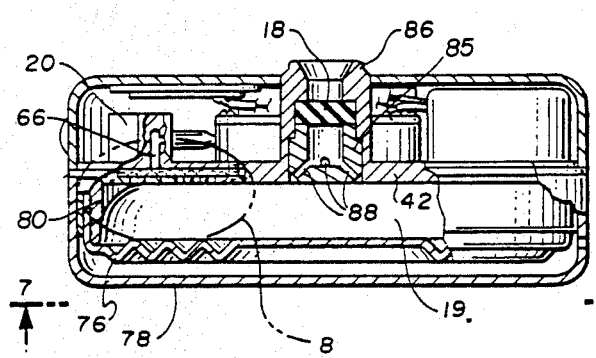
FIG. 6 is a cutaway elevational view of the drug administration device taken along lines 6—6 of FIG. 2.
Figure 7:
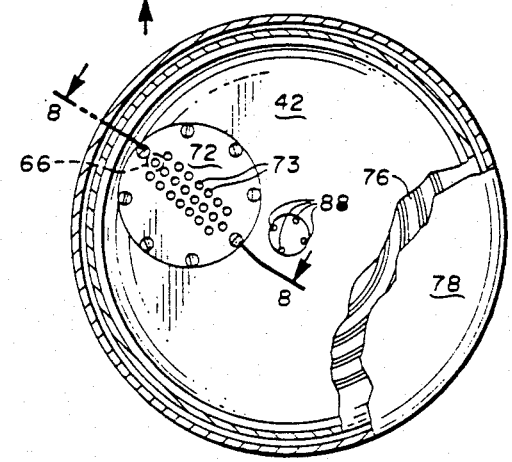
FIG. 7 is a cutaway bottom plan view of the drug administration device with part cutaway to reveal the reservoir and associated elements thereof.
Figure 8:
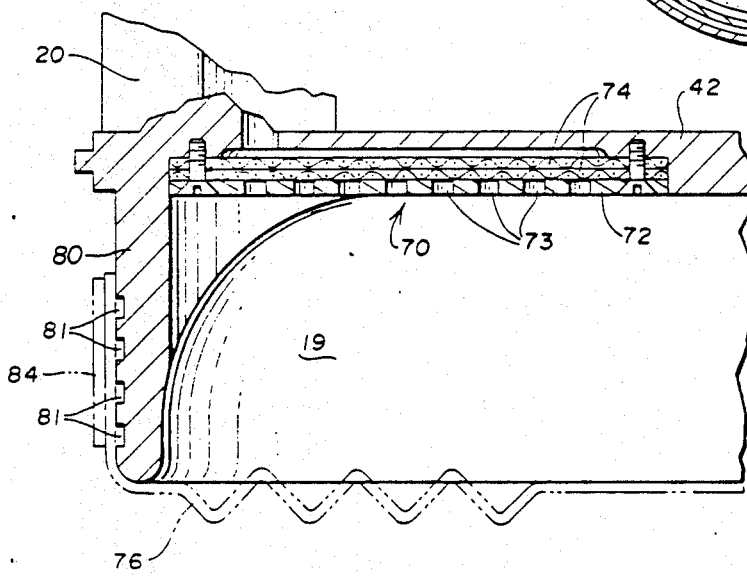
FIG. 8 is a sectional view of the filter taken along lines 8—8 of FIG. 7, and a detail of FIG. 6 taken at 8 thereof and shown in enlarged scale.

Pump 44 is connected to catheter port 20, which provides an outlet conduit 62 which is connected to catheter 22, which can be screwed onto port 20, and receives its input from an inlet conduit 64, which is connected to an inlet port 66, which communicates with the fluid reservoir 19 through a filter 70 shown in FIG. 7 and in cross section in FIGS. 6 and 8. As shown in FIG. 8, the filter 70 is comprised of a clamping ring and screen 72 which has a number of holes 73 therein for permitting the flow of a liquid therethrough. The clamp ring and screen 72 holds a pair of fine filters 74 for screening out any particles of skin or hair which could have reached the fluid reservoir 19 when the reservoir is filled utilizing a hypodermic needle inserted through the patient's skin.

The reservoir 19 is formed with its top portion being the underside of housing 42, and its lower portion formed from a flexible diaphragm. The flexible diaphragm 76 is protected by a lower shield 78, which forms a seal against a projecting flange 80, which has a plurality of circumferential sealing grooves 81, which projects from housing 42. The upper shield portion 24 is also seated against the flange 80. The diaphragm is secured to the housing 42 with a circumferential Teflon band 84 and a suitable adhesive to form a sealed reservoir.

Figure 5:
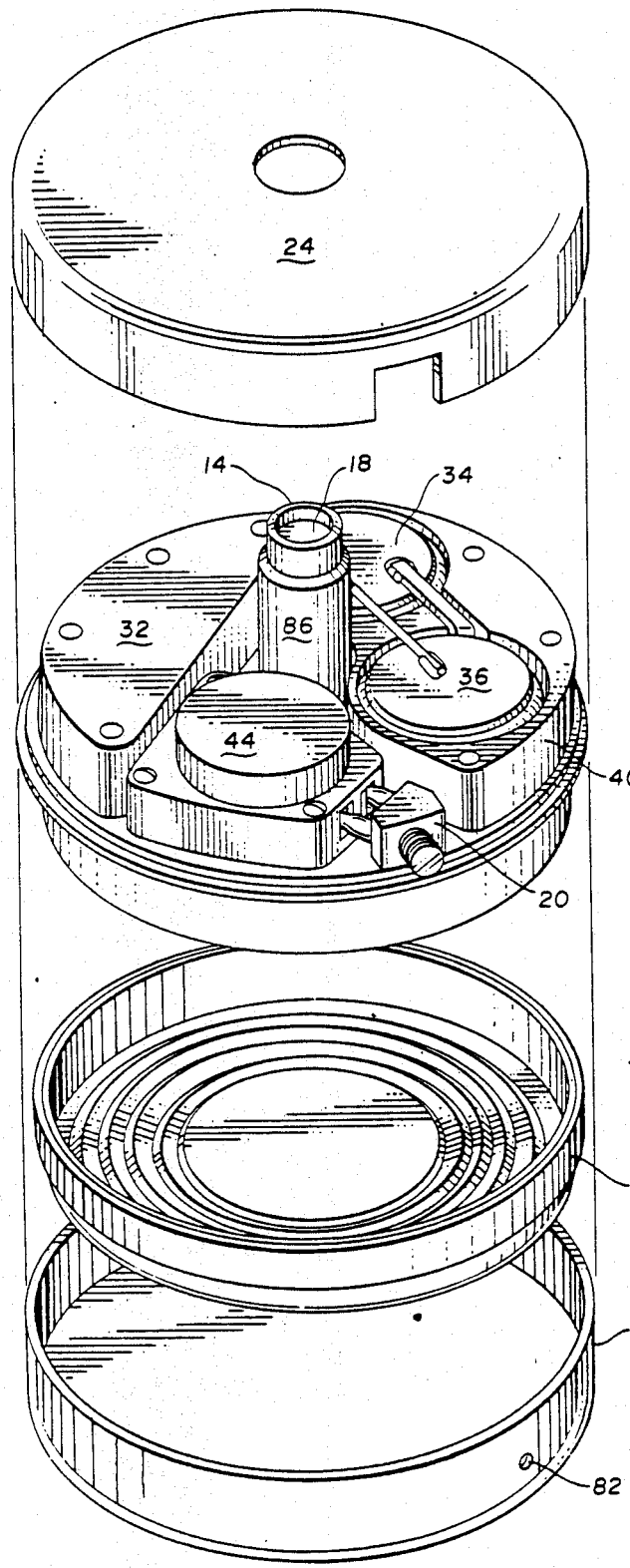
FIG. 5 is an exploded view of the drug administration device with catheter not shown.
Figure 2:
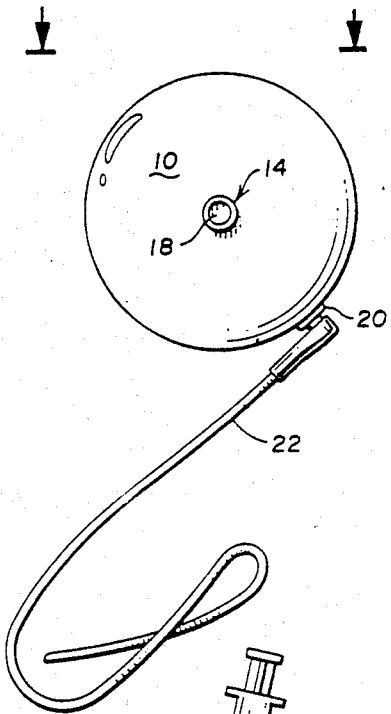
FIG. 2 is a plan view of the drug administration device of FIG. 1.

After the sealed reservoir 19 has been formed, and lower shield 78 has been positioned against flange 80 of housing 42, the space between diaphragm 76 and the lower housing 78 is evacuated through the hole 82 shown in FIG. 5, and a small amount of a suitable fluorocarbon liquid is inserted in the hole to backfill the device. The hole 82 is then welded to seal the unit. In one embodiment, approximately 2.5 CCs of Fluorinert FIC88 is inserted in the unit. The amount of fluorocarbon fluid, or other suitable volatile fluid is selected to provide a positive pressure against bellows 76 when the administration device is implanted in the patient's body. As is well-known in the art such a volatile fluid exerts a constant vapor pressure at a given temperature regardless of volume. Thus, the constant positive pressure compresses bellows 76 and urges the liquid contents of the reservoir 19 through the filter 70. The fluid is forced through the screen 72 and the filter segments 74 to the input port 66 of pump 56. As pump 56 rotates, the rolling action of rollers 54 at the ends of arm 52 allows a predetermined amount of liquid to be either pumped or metered from reservoir 19 through the catheter 22 to the location within the body where it is desired to apply the medical fluid.

The fluid supply in the reservoir is periodically replenished by applying a hypodermic needle 16 as shown in FIG. 1. The hypodermic needle pierces the septum 18. As shown in FIG. 6, the septum 18 is seated against a plug 84. The plug 84 and septum 18 are mounted in a projecting neck portion 86 of the housing 42. Neck portion 86 has a central opening to permit access to septum 18 by hypodermic needle 16. Needle 16 is forced through the septum 18, which may be formed of a silicone rubber compound. If the hypodermic needle 16 has a rounded blunt tip and a delivery port located on the shaft of the needle, the insertion of the needle through the septum 18 will not cause a permanent hole to form in septum 18. After the hypodermic needle has been forced through the septum, its contents are delivered into the chamber in plug 84 under pressure when the pressure of its contents exceeds the pressure of reservoir 68, which is typically 3 to 5 psi. The fluid is forced into reservoir 68 through apertures 88 in plug 84, and bellows 76 is expanded to accept the fluid. The hypodermic needle is then withdrawn and the silicone rubber of septum 18 reseals.

Turning now to the electrical schematic of FIGS. 11A and 11B, the detailed circuitry of electronic module 32 is shown. Batteries 34 and 36 apply a fixed voltage to the constant current source circuit of transistors Q1 and Q2, which provides a constant current to the individual circuit elements within electronic module 32 to minimize drain on batteries 32 and 34. The reed switch 89 is encapsulated in the electronic module, and is actuated by the presence of a magnet, or a programming device, in contact with the patient's skin in the vicinity of the drug administration device.

As reed switch 89 is closed, a positive voltage is connected to the $\overline{INT}$ input at pin 36 of microprocessor 100. The closing of reed switch 89 by the magnet or programmer also applies power to the receiver circuit 101, comprised of transistors Q5 through Q8. Receiver circuit 101 is a part of the electronic module 32 as is the antenna ANT. The antenna is a 1 mh ferrite core antenna which is also a part of the electronic module 32. The antenna is tuned with a capacitor C6 for receipt of the 175 KC carrier programming signal pulses from the programmer.

The entirety of the circuit in the receiver or demodulator 101 is the same as used in the Medtronic 5995 programmable Xyrel ® pacemaker.

Programming command information is applied to the drug administration device by a programmer which has electrical operating characteristics identical to those of the Medtronic 9600 Rate Controller programmer. The programming command information is applied by setting the selector switch of the programmer to a position corresponding to a dosage command between 1 and 7 to be applied and pressing the push button corresponding to the "Activate A Switch" of the Model 9600 Programmer to deliver two bursts of between 1 and 7 pulses of 175 KC carrier. The pulses have a nominal duration of 1.5 msec, and a period of 3.0 msec. The two bursts or groups of N pulses which can be referred to as $N_1$ and $N_2$ are separated by at least 2.5 msec. At least 13 msec shall separate different groups of two bursts. The command programmer produces 1 to 7 $N_1$ pulses to program dosage commands and 1 to 7 $N_2$ pulses to program interval commands. A "make permanent" command to make the dosage and interval commands permanent is generated by transmitting $N_1$ and $N_2$ bursts of 8 pulses.

The "personality" of the drug administration device can be altered using a special programmer having extended capabilities for the number of pulses generated in $N_1$ and $N_2$. The device is placed in the motor parameter subroutine made by causing the programmer to generate a 9 pulse $N_1$ burst and an arbitrary number of $N_2$ pulses. After enabling the new parameter mode, the device accepts the new parameters from $N_1$ and $N_2$ bursts of 1 to 16 pulses as indicated in Table 1 below:

| Group | $N_1$ | $N_2$ | Result |
|---|---|---|---|
| 1 | 9 | 1 to 7 | Enables new motor parameter mode |
| 2 | 1 to 16 | 1 to 16 | Receives 8 bit word to determine pulse width |
| 3 | 1 to 16 | 1 to 16 | Receives 8 bit word to determine motor pulse period |
| 4 | 1 to 16 | 1 to 16 | Receives 16 bit word to store data to characterize dosage to be dispensed in response to an $N_1$ burst of one pulse. |
| 5 | 1 to 16 | 1 to 16 | |

The $N_1$ burst in groups 2 and 3 carries the most significant nibble of the 8 bit word and $N_2$ indicates the least significant nibble. Group 4 carries the most significant nibble of the most significant byte in $N_1$ and the least significant nibble in $N_2$. Similarly, group 5 transmits the most and least significant nibbles of the least significant byte in bursts $N_1$ and $N_2$. Similar 16 bit words are received for the dosage data to be stored relative to dosage commands from 2 through 7.

The special programmer allows changing the personality of the device over a wide range. The motor pulse width can, in one embodiment, be varied in approximately 1 msec intervals from 1 msec minimum to 250 msec maximum. The delay between motor pulses can be varied in one embodiment between 5.86 msec minimum to 568 msec maximum with approximately 2.2 msec between choices. The number of pulses delivered to the stepper motor at each of the command dosages can be varied from 0 to 65,535.

Using the command programmer and a typical device "personality" 7, drug dosages can be selected from a zero dosage to a 1.0 ml dosage with 0.1 ml increments between choices. The time interval between dosages can be selected between 1 and 12 hours in 7 choices. With the preferred embodiment shown and a motor pulse period of 33 ms, the rate at which the drug is dispensed is 1 ml per 39.6 minutes.

Circuit 101 operates to apply a positive pulse to pin 23 of microprocessor 100 at the $\overline{EF2}$ input each time a carrier pulse is received. Circuit 101 also applied at pin 22 of microprocessor 100, an $\overline{EF3}$ input during the time that the first group of pulses corresponding to the dosage are applied. After the dosage command has been applied, the selector switch of the programmer is moved to a position to select the time interval command for administration of the selected dosage and the button is again pressed, and the pulses are applied to the $\overline{EF2}$ input and the envelope for the train of pulses is applied to the $\overline{EF3}$ input. The input commands are tested and stored as explained below in connection with the description of the programming. After the desired input command has been applied, it can be made permanent by depressing the switch corresponding to the "Interlock 30 Switch" of the Model 9600 programmer, and then depressing the "Activate A Switch" twice to transmit a "Make Permanent" command. The description of the programming below illustrates how the circuit module 32 functions upon receipt of the "Make Permanent" command.

A clock input to the microprocessor 100 is supplied by a 32.768 KHz crystal 101a connected as shown in FIG. 11A, with its associated capacitor C9 and resistor R16.

A connection is made from the CLR input at pin 3 of microprocessor 100 to an output pin 4 of the electronic module 32 to permit grounding of the CLR input to microprocessor 100. Grounding the reset pin 4 of module 32 resets the microprocessor program counter to position zero, and provides a convenient and direct means of restarting the programming on the bench when the reset pin of the module is accessible.

The other connections to the microprocessor at pins 40 and 16 to apply the DC power are standard, and the unused logic inputs at pins 37, 38, 2, and 21, are all tied back to the DC supply through R18.

The microprocessor 100 is connected to a memory 102, which in the embodiment shown, is divided between a 512 byte ROM memory 102a and a 128 byte RAM memory 102b. The information in the RAM memory is modified by the external programmer, while the information stored in the ROM, which relates to the programming, is not varied, and is preloaded at the time the device is assembled.

Electronic module 32 drives either the acoustic transducer 26 from pin 9, or the winding of stepper motor 46 from pins 10 and 11. The circuitry of gates A4 through A7 function to enable either the acoustic transducer or the stepper motor winding to accept outputs from the microprocessor. Operation of the circuitry of gates A4 through A7 is discussed in more detail below in connection with the operation of the programming of the device.

In one embodiment, the following values were used for the components of the electronic module 32:

| | |
|---|---|
| $Q_1$, $Q_2$ | 2N3799 |
| $Q_5$, $Q_6$, $Q_7$, $Q_8$ | 2N2484 |
| $B_1$ | 2N6459 |
| $R_1$, $R_5$, $R_6$, $R_{14}$, $R_{17}$ | 10 M |
| $R_2$ | ADJUST FOR CURRENT OF 45 μA |
| $R_7$ | 200K |
| $R_8$, $R_{13}$ | 20 M |

-continued

| | |
|---|---|
| $R_9$ | 3.5 M |
| $R_{10}$, $R_{15}$ | 100K |
| $R_{11}$ | 15K |
| $R_{12}$ | 300K |
| $R_{16}$ | 12 M |
| $R_{18}$ | 1 M |
| $C_1$ | 10 μf |
| $C_2$ | 120 pf |
| $C_3$ | .047 μf |
| $C_4$, $C_5$, $C_9$ | 330 pf |
| $C_6$ | 630 pf |
| $C_7$ | 330 pf |
| $C_8$ | .001 μf |
| $A_4$, $A_7$ | CD4013 |
| $A_5$, $A_6$ | CD 4011 |

Simplified Description of Operation

The drug administration device operates to dispense selected doses of a medical fluid at selected time intervals. The external programmer sends a group of 1 to 7 pulses to designate the dosage to be administered and another group of 1 to 7 pulses to designate the time interval. The pulses indicate the location within memory where the parameter signals to determine the number of pulses to determine the dosage and to determine the time between dosages are stored.

A device personality programmer in contrast to the above-described physician operated external programmer is used to set certain implantable device characteristics. This may be done either at the time of manufacture or after the device has been implanted in a patient without removal of the device. The stepper motor pulse width, the delay time between stepper motor pulses and the number of stepper motor pulses to be dispensed for each of the seven dosage commands are all remotely programmable with the personality programmer.

Once each second, the device checks to determine if a magnet or a programmer has been placed over the implanted device. When a magnet or programmer is detected, the dispensing of the drug is immediately inhibited and the acoustic transducer indicates the 1 to 7 pulses which were previously set in for the dosage and interval. The programmer can then be used to apply new code pulses which are read back on the acoustic transducer. The operating codes are stored in the device until a separate "Make Permanent" code is received to cause the device to operate under control of the new commands.

Description of Program Flow Charts

Figure 12:
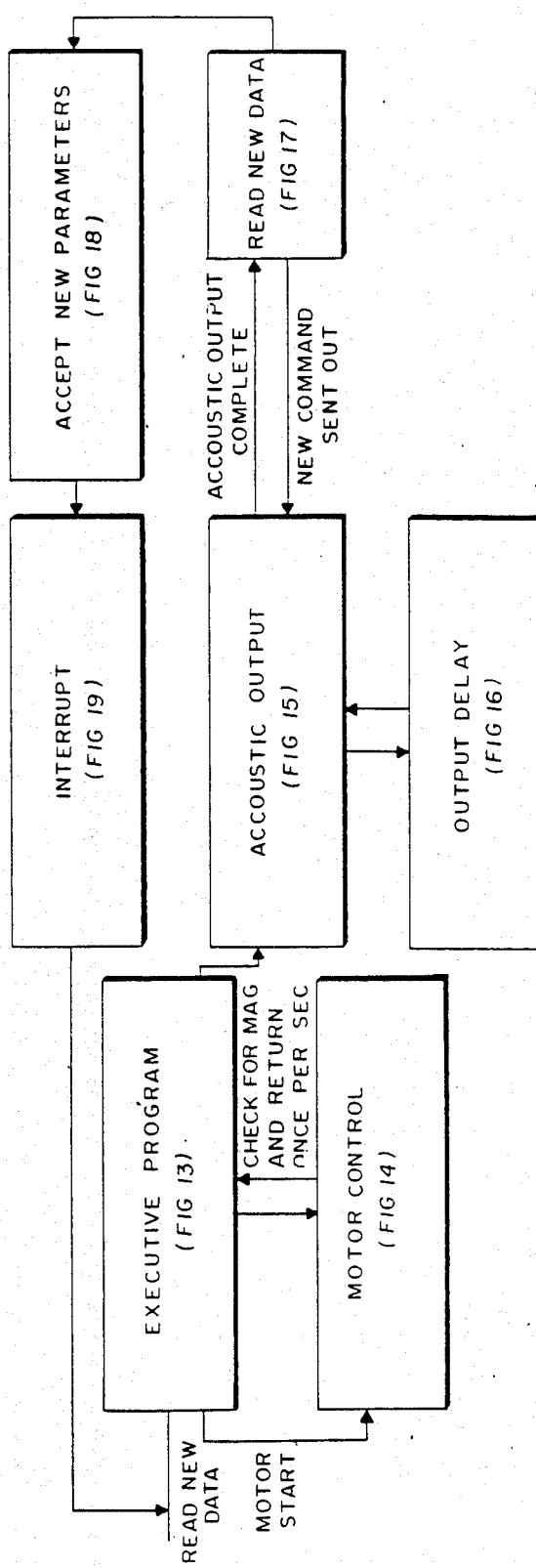
FIG. 12 is a block diagram of the programming of the drug administration device showing the interrelationship of the executive program and the various subroutines shown in FIGS. 13 through 19.

There is shown in FIG. 12 a flow diagram of the steps for implementing the programming of the drug administration device, the circuit connections for which are shown in FIG. 11. In one illustrative embodiment of this invention, the microprocessor 100 includes a plurality of pointer registers for storing pointers or addresses to word locations within the ROM portion 102B of the memory 102. In this illustrative embodiment, there are included within the microprocessor 100 the following registers for storing the indicated pointers or addresses:

R(0) = Working Data Temporary Storage Counter
R(1) = Interrupt Subroutine Program Counter
R(2) = Dummy "X" Register
R(3) = Accoustic Output Subroutine Program Counter
R(4) = Executive Program Counter
R(5) = Variable Delay Counter
R(6) = Data Temporary Storage
R(7) = Dosage/Interval Flag
R(8) = One Second Delay Counter
R(9) = Motor Control Subroutine Program Counter
R(A) = Permanent Data ROM Memory Pointer
R(B) = Just Sent Data RAM Memory Pointer
R(C) = Read New Data Counter
R(D) = Number Of Seconds Delay Counter
R(E) = Previously Sent Data Memory Pointer
R(F) = Working Data Pointer Further, the flag inputs for the reed switch $\overline{(EF1)}$ and the data pulse $\overline{(EF1)}$ and the data pulse envelope $\overline{(EF3)}$ are applied to the microprocessor as shown and described with regard to FIG. 3. The notation for the flag inputs and the pointers and counters is used throughout the program listing set out below. As is conventional with microprosessors, the microprocessor 100 includes an address counter 107, which increments one for each step of the program as it is carried out under the control of the microprocessor 100 to designate the next location within the memory 102 from which information is to be read out. The steps to be explained with respect to FIG. 12 to effect a programmable drug administration device were implemented using an RCA COSMAC microprocessor by the following machine instructions:

| Step Location | Symbolic Notations | | | Remarks |
|---|---|---|---|---|
| 200 | DIS | ,#00 | | ..DISABLE THE INTERUPT ..INPUT |
| 202 | LDI | A.1(START);PHI | 4 | ..INITIALIZE R4 AS EXE- |
| | LDI | A.0(START);PLO | 4 | ..CUTIVE PROGRAM ..COUNTER |
| | LDI | A.1(INTER);PHI | 1 | ..R1 AS THE INTERUPT |
| | LDI | A.0(INTER);PLO | 1 | ..SUBROUTINE POINTER ..AND COUNTER |
| | LDI | A.1(MOTOR);PHI | 9 | ..R9 AS THE MOTOR ..CONTROL |
| | LDI | A.0(MOTOR);PLO | 9 | ..SUBROUTINE POINTER ..AND COUNTER |
| | LDI | A.1(OUTPUT);PHI | 3 | ..R3 AS THE ACOUSTIC |
| | LDI | A.0(OUTPUT);PLO | 3 | ..OUTPUT SUBROUTINE ..POINTER AND COUNTER |
| | LDI | A.1(READND);PHI | C | ..RC AS THE READ NEW ..DATA |
| | LDI | A.0(READND);PLO | C | ..SUBROUTINE POINTER ..AND COUNTER |
| | LDI | A.1(SECDEL);PHI | 5 | ..R5 AS THE .7 SECOND |
| | LDI | A.0(SECDEL);PLO | 5 | ..DELAY SUBROUTINE ..POINTER AND COUNTER ..(FOR OUTPUT SUB) |
| | LDI | A.1(STAOS);PHI | 6 | ..R6 AS THE OUTPUT |

| Step Location | Symbolic Notations | | | Remarks |
|---|---|---|---|---|
| | LDI | A.0(STAOS);PLO | 6 | ..FORMAT TABLE POINTER |
| | LDI | #04;PHI | A | ..RA AS THE PERMANENT |
| | LDI | #00;PLO | A | ..DATA RAM POINTER |
| | LDI | #04;PHI | B | ..RB AS THE JUST SENT |
| | LDI | #02;PLO | B | ..DATA RAM POINTER |
| | LDI | #04;PHI | E | ..RE AS THE PREVIOUSLY |
| | LDI | #04;PLO | E | ..SENT DATA RAM POINTER |
| | LDI | #01;STR | A;INC A | ..SET DOSAGE AND |
| | | | | ..INTERVAL TO A 1,1 |
| | | | | ..STATE |
| | STR | A;DEC | A | |
| | SEP | 4 | | ..CALL EXECUTIVE |
| | | | | ..PROGRAM |
| | | | Executive Program. | |
| 204 | START: SEP | 9 | | ..CALL MOTOR CONTROL |
| | | | | ..SUBROUTINE |
| 205 | BN1 | START | | ..CHECK FOR MAGNET-NO |
| | | | | ..GO TO START |
| 252 | LDI | #04;PHI | F | ..POINT RF TO RAM TO |
| | LDI | #06;PLO | F | ..HOLD PRESENTLY WORK- |
| | STR | B;INC B; | | ..ING MOTOR CONTROL |
| | STR | B;DEC B | | ..PARAMETERS |
| | GLO | 9;STR F; | | |
| | INC | F | | |
| | GHI | D;STR F; | | |
| | INC | F | | |
| | GLO | D;STR F; | | |
| | INC | F | | |
| | GLO | A;STR F | | |
| 254 | LDI | #00;PLO | A | ..POINT RA TO BEGINNING |
| | | | | ..OF PERMANENT DATA RAM |
| | LDA | A | | ..AND PLACE THE CON- |
| | STR | E;INC E | | ..TENTS INTO RE TO |
| | | | | ..SEND OUT DATA |
| | LDN | A;DEC A | | |
| | STR | E;DEC E | | |
| 256 | CJSENT: SEP | 3 | | ..CALL ACOUSTIC OUTPUT |
| | | | | ..SUBROUTINE |
| 314 | SEP | C | | ..CALL READ NEW DATA |
| | | | | ..SUBROUTINE |
| 354 | LDN | B | | ..CHECK JUST SENT DATA |
| | XRI | #09 | | ..IF ACCEPT NEW DATA |
| | | | | ..CODE |
| | LBZ | ACEPTD | | ..YES BRANCH TO ACCEPT |
| | | | | ..NEW DATA |
| 388 | LDN | B | | ..CHECK JUST SENT DATA |
| | XRI | #08 | | ..IF PERMANENT CODE |
| | BNZ | SENOUT | | ..NO GO TO SEND OUT |
| | | | | ..DATA |
| 390 | INC | B | | |
| | LDN | B;DEC B | | |
| | XRI | #08 | | |
| | BZ | SETPER | | ..YES SET NEW DATA TO |
| | | | | ..PERMANENT |
| | SENOUT: LDA | B | | ..LOAD JUST SENT DATA |
| | | | | ..FROM RB |
| | STR | E;INC E | | ..TO PREVIOUSLY SENT |
| | | | | ..DATA LOCATION |
| | LDN | B;DEC B | | ..AND BRANCH TO CALL |
| | | | | ..OUTPUT |
| | STR | E;DEC E | | |
| | BR | CJSENT | | |
| 394 | SETPER: LDA | E | | ..LOAD PREVIOUSLY SENT |
| | | | | ..DATA |
| | STR | A;INC A | | ..INTO THE PERMANENT |
| | | | | ..DATA LOCATION |
| | LDN | E;DEC E | | |
| | STR | A;DEC | | |
| 396 | WAITMA: SEP | C | | ..CALL READ NEW DATA |
| | | | | ..SUBROUTINE |
| | BR | WAITMA | | ..AND WAIT FOR INTER- |
| | | | | ..RUPT |
| | | | Interrupt Subroutine. | |
| 402 | INTER: LDI | A.0(SINTER) | | ..SET UP R4 TO RETURN |
| | | ;PLO 4 | | ..CONTROL TO MAIL PRO- |
| | LDI | A.0(READND) | | ..GRAM COUNTER |
| | | ;PLO C | | |
| | SEP | 4 | | ..RC TO BEGINING OF |
| | | | | ..READ NEW DATA SUB |

-continued

| Step Location | Symbolic Notations | | | Remarks |
|---|---|---|---|---|
| 404 | SINTER: | LDI | A.0(INTER); PLO 1 | ..RESTORE INTERUPT SUB- ..ROUTINE |
| 408 | | LDN | B | ..CHECK IO SEE IF JUST ..DATA |
| | | BZ | #08 | ..IS ZERO YES RESTART ..PROGRAM |
| | | XRI | #08 | ..CHECK JUST SENT DATA ..IF PERMANENT |
| | | BNZ | CONMOT | .CODE NO GO TO CONTINUE ..MOTOR SUB |
| | | INC | B | |
| | | LDN | B;DEC B | |
| | | XRI | #08 | |
| | | BZ | RESETM | ..YES GO TO RESET MOTOR ..SUB |
| 414 | CONMOT: | LDI | #04;PHI F | ..POINT RF TO RAM TO ..RETRIEVE |
| | | LDI | #06;PLO F | ..PRESENTLY WORKING ..MOTOR CONTROL |
| | | LDA | F;PLO 9 | ..PARAMETERS |
| | | LDA | F;PHI D | |
| | | LDA | F;PLO D | |
| | | LDN | F;PLO A | |
| 424 | | SEX | 2;OUT 1 | ..SET OUTPUT PORT TO ..MOTOR |
| | | BR | START | ..GO TO MOTOR CONTROL ..SUBROUTINE |
| 426 | RESETM: | LDI | A.1(MOTOR); PHI 9 | ..RESTORE MOTOR CONTROL ..SUBROUTINE |
| | | LDI | A.0(MOTOR); PLO 9 | |
| 428 | | LDI | #00;PLO A | ..RESTORE PERMANENT ..DATA POINTER |
| | | LDA | A;STR E; INC E | ..LOAD NEW PERMANENT ..DATA INTO RE |
| | | LDN | A;STR E; DEC E;DEC A | ..TO SEND OUT NEW ..PARAMETERS |
| | | SEP | 3 | ..CALL ACOUSTIC OUTPUT ..SUBROUTINE |
| 428 | | BR | START | ..GO TO MOTOR CONTROL ..SUBROUTINE |
| | Motor Control Subroutine. | | | |
| 206 | MOTOR: | SEX | 2:REQ;OUT 1 | ..SET OUTPUT PORT TO ..MOTOR |
| 208 | | LDI | A.1(INTTAB) ;PHI F | ..POINT RE TO BEGINNING ..OF INTERVAL TABLE |
| | | LDI | A.0(INTTAB) ;PLO F | |
| | | LDI | #04;PHI 0 | ..POINT R0 TO PULSE |
| | | LDI | #70;PLC 0 | ..WIDTH AND PULSE ..INTERVAL TABLE |
| | | INC | A | ..POINT RA TO INTERVAL ..# IN RAM |
| | | LDN | A;SHL;STR B | ..GET # MULT. BY 2 ..(TABLE 2 BYTES LONG) |
| | | DEC | A | ..POINT RA TO DOSAGE # ..IN RAM |
| | | SEX | B;GLO F; ADD | ..INCREMENT INTERVAL ..TABLE POINTER |
| | | PLO | F;SEX F | ..BY # GENERATED FROM ..INTERVAL # |
| | | LDXA | ;PHI D | ..GET INTERVAL DELAY # |
| | | LDX | ;PLO D | ..FROM TABLE AND LOAD ..INTO DELAY SUB |
| 210 | CTR2: | SEP | 4 | ..GO TO EXEC. PROG. AND ..CHECK FOR MAG. |
| 212 | | LDI | #02 | ..LOAD BASIC DELAY # |
| | | PHI | 8 | ..FOR 1 SEC. |
| 214 | CTR1; | DEC NOP | 8;GHI 8 | |
| 216 | CTR3: | BNZ | CTR1 | ..CHECK IF 1 SEC. DELAY ..DONE |
| 218 | | DEC | D;GHI D | |
| 220 | | BNZ | CTR2 | ..CHECK IF INTERVAL |
| | | GLO | D | ..DELAY DONE |
| | | BNZ | CTR2 | |
| 222 | | LDI | #04;PHI F | ..POINT RF TO DOSAGE ..TABLE IN RAM |
| | | LDI | #60;PLO F | |

| Step Location | Symbolic Notations | | | Remarks |
|---|---|---|---|---|
| | | LDN | A;SHL;STR B | ..GET DOSAGE # MULT. BY ..2 |
| | | SEX | B;GLO F; ADD | ..INCREMENT DOSAGE ..TABLE POINTER |
| | | PLO | F;SEX F | ..BY # GENERATED FROM ..DOSAGE # |
| | | LDXA | ;PHI D | ..LOAD DOSAGE # FROM ..TABLE |
| | | LDX | ;PLO D | ..INTO MOTOR PULSE SUB ..COUNTER |
| 224 | CHECKD: | GHI | D | |
| | | BNZ | PM | ..CHECK IF DOSAGE DONE |
| | | GLO | D | |
| | | LBZ | MOTOR | |
| 230 | PM: | DEC | D | |
| | | LDA | 0 | ..LOAD MOTOR PULSE ..WIDTH DELAY # |
| 232 | | SEQ | | ..PULSE MOTOR |
| 234 | | BZ | MPWD1 | ..IF PULSE WIDTH DELAY |
| | MPWD: | SMI | #01 | ..0 GO TO PULSE INTER- ..VAL, ELSE DEC. COUN- ..TER |
| 236 | | BNZ | MPWD | ..UNTIL 0 THEN GO TO ..PULSE INTERVAL |
| 238 | MPWD1: | REQ | | ..STOP PULSE MOTOR |
| 240 | | SEP | 4 | ..CHECK FOR MAGNET |
| 242 | | LDA | 0 | ..LOAD PULSE INTERVAL |
| | | DEC | 0 | ..DELAY #. POINT R0 |
| | | DEC | 0 | ..BACK TO PUSLE WIDTH ..DELAY # IN RAM. |
| 244 | | BZ | CHECKD | ..CHECK PULS. INT. DEL. ..0 GO TO PULSE MOT. |
| 246 | | PLO | 8 | ..OTHERWISE DELAY ..BETWEEN PULSES |
| 248 | RECMOT: | DEC | 8;GLO 8 | |
| | | NOP | | |
| 250 | | BNZ | RECMOT | |
| | | BR | CHECKD | |
| | Output Delay Subroutine. | | | |
| 312 | EXIT4: | SEP | 3 | ..EXIT SECOND DELAY SUB ..TO OUTPUT SUB |
| 300 | SECDEL: | LDX | ;PLO D | ..LOAD # OF UNIT TIMES ..DELAY FROM TABLE |
| 302 | PDS1: | LDI | #01;PHI 8 | ..LOAD UNIT TIME # ..INTO COUNTER |
| 304 | PDS2: | DEC | 8;GHI 8; NOP | |
| 306 | | BNZ | PDS2 | ..CHECK UNIT TIME DELAY ..DONE |
| 308 | | DEC | D;GLO D | |
| 310 | | BNZ | PDS1 | ..CHECK # OF UNIT TIME ..DELAYS IS 0 |
| 312 | | BR | EXIT4 | ..IF 0 EXIT BACK TO ..OUTPUT SUB |
| | Acoustic Output Subroutine. | | | |
| 299 | EXIT2: | DEC | 6;DEC 6 | ..WHEN EXITING, RESET R6 |
| | | DEC | E;DEC E; | ..TO BEGINNING OF OUT- ..PUT FORMAT TABLE |
| 301 | | SEP | 4 | ..CALL EXEC. PROGRAM |
| 258 | OUTPUT: | LDI | #01;PLO 7 | ..SET DOSAGE INTERVAL ..FLAG TO DOSAGE |
| 260 | | SEX | 2;OUT 2 | ..SET OUTPUT PORT TO ..ACOUSTIC |
| | | SEX | 6 | |
| 262 | | SEQ | | ..TURN ON TONE |
| 264 | | SEP | 5 | ..CALL OUTPUT FORMAT ..DELAY FOR ALERT TONE |
| 266 | | REQ | | ..TURN OFF TONE |
| 268 | | IRX;IRX | | ..SET R6 TO OFF DELAY # |
| 270 | AOS9: | SEP | 5 | ..CALL OUTPUT FORMAT ..DELAY |
| 272 | | LDA | E;PLO 2 | ..LOAD DOSAGE # INTO ..TONE COUNTER |
| 274 | AOS6: | BZ | AOS7 | ..CHECK TONE COUNTER 0, ..NO CONTINUE |
| 276 | | DEC | 2 | ..DEC TONE COUNTER |
| 278 | | SEQ | | ..TURN ON TONE |
| 280 | | SEP | 5 | ..CALL TONE DELAY SUB |
| 282 | | REQ | | ..TURN OFF TONE |

-continued

| Step Location | Symbolic Notations | | | Remarks |
|---|---|---|---|---|
| 284 | | SEP | 5 | ..CALL OFF TONE DELAY ..SUB |
| 286 | AOS7: | GLO | 2 | |
| 288 | | BNZ | AOS6 | ..CHECK IF TONE COUNTER ..0, NO REPEAT |
| 290 | | GLO | 7 | |
| | | BZ | EXIT2 | ..CHECK BOTH DOSAGE AND ..INTERVAL DONE |
| 294 | | DEC | 7;DEC 6 | |
| 296 | | SEP | 5 | ..OUTPUT DOSAGE/INTER- ..VAL SPACE OFF TONE |
| 298 | | INC | 6 | |
| | | BR | AOS9 | ..CONTINUE OUTPUTING ..INTERVAL TONES |
| | Read New Data Subroutine. | | | |
| 350 | EXIT 3: | SEP | 4 | ..RETURN TO EXECUTIVE ..PROGRAM |
| 318 | READND: | SEX | C;RET ,#2C | ..ENABLE INTERUPT ..INPUT |
| 319 | | LDI | #00 | ..CLEAR COUNTER FOR ..SERIAL BIT WORD |
| 320 | STARTR: | B3 | STARTR | ..WAIT FOR FIRST WORD ..(DOSAGE) |
| 322 | READDO: | B2 | CECKW1 | ..CHECK FOR END OF ..FIRST WORD |
| 324 | | ADI | #01 | ..INCREMENT COUNTER ..FOR EACH BIT |
| | | BR | STARTR | ..CONTINUE COUNTING ..BITS OF FIRST WORD |
| 328 | CECKW1: | BN3 | READDO | ..IF FIRST WORD DONE |
| 330 | | STR | B;INC B | ..STORE FIRST WORD IN ..RAM IN JUST SENT ..LOCATION |
| 332 | | LDI | #00 | ..CLEAR COUNTER FOR ..SECOND WORD (INTERVAL) |
| 334 | STARRE: | B3 | STARRE | ..WAIT FOR SECOND WORD |
| 336 | READIN: | B2 | CECKW2 | ..CHECK FOR END OF ..SECOND WORD |
| 338 | | LDI | #01 | ..INCREMENT COUNTER FOR ..EACH BIT |
| | | BR | STARRE | ..CONTINUE COUNTING ..BITS OF SECOND WORD |
| 342 | CECKW2: | BN3 | READIN | ..IF SECOND WORD DONE |
| 344 | | STR | B;DEC B | ..STORE SECOND WORD IN ..RAM IN JUST SENT ..LOCATION |
| 346 | | SEX | C | |
| 348 | | DIS | ,#2C | ..DISABLE INTERRUPT ..INPUT |
| 350 | | BR | EXIT3 | ..GO TO EXIT TO RETURN ..TO EXEC. PROGRAM |
| | Accept New Parameters Subroutine. | | | |
| 356 | ACEPTD: | LDI | #04;PHI 0 | ..CLEAR LOCATION 0 OF |
| | | LDI | #60;RNO 0 | ..DOSAGE TABLE IN RAM |
| | | LDI | #00 | ..TO GET READY TO AC- ..CEPT NEW PARAMETERS |
| | | STR | 0 | |
| | | INC | 0 | |
| | | STR | 0 | |
| 358 | | LDI | #71;PLO 0 | ..POINT R0 TO PULSE ..INTERVAL RAM ..LOCATION |
| 360 | | LDI | #00 | ..LOAD 0 INTO JUST |
| | | STR | B | ..SENT RAM TO CHECK ..FOR DATA RECEIVED ..LATER |
| 362 | DATA1: | SEP | C | ..CALL READ NEW DATA TO |
| | | SEX | B | ..GET FIRST BYTE WHICH ..IS THE PULSE INTER- ..VAL # |
| 364 | | LDI | #03 | ..WE MUST SUBTRACT 1 ..FROM EACH HEX |
| | | SD | | ..AND THEN COMBINE THE ..TWO HEX DIGITS |
| | | STR | B | ..TO GET ONE HEX BYTE. ..R0 POINTS TO |
| | | IRX | | ..THE RAM LOCATION ..WHERE THE BYTE WILL |
| | | LDI | #01 | ..BE PLACED THIS |

| Step Location | Symbolic Notations | | Remarks |
|---|---|---|---|
| | | | ..PROCESS IS REPEATED |
| | SD | | ..UNTIL A NEW PULSE |
| | | | ..WIDTH BYTE AND A |
| | STR | B | ..NEW PULSE INTERVAL |
| | | | ..AND NEW DOSAGE |
| | DEC | B | ..BYTES ARE RECEIVED OR |
| | LDA | B | ..INTERUPT OCCURS |
| | SHL | | |
| | SHL | | |
| | SHL | | |
| | SHL | | |
| | ADD | | |
| | DEC | B | |
| | STR | 0 | |
| | DEC | 0 | |
| | GLO | 0 | |
| | XRI | #61 | |
| | BZ | STOPDA | |
| 366 | BR | DATA1 | |
| | STOPDA: LBR | #0008 | ..RESTART ENTIRE PRO- |
| | | | ..GRAM |
| | END | | |

Figure 13:
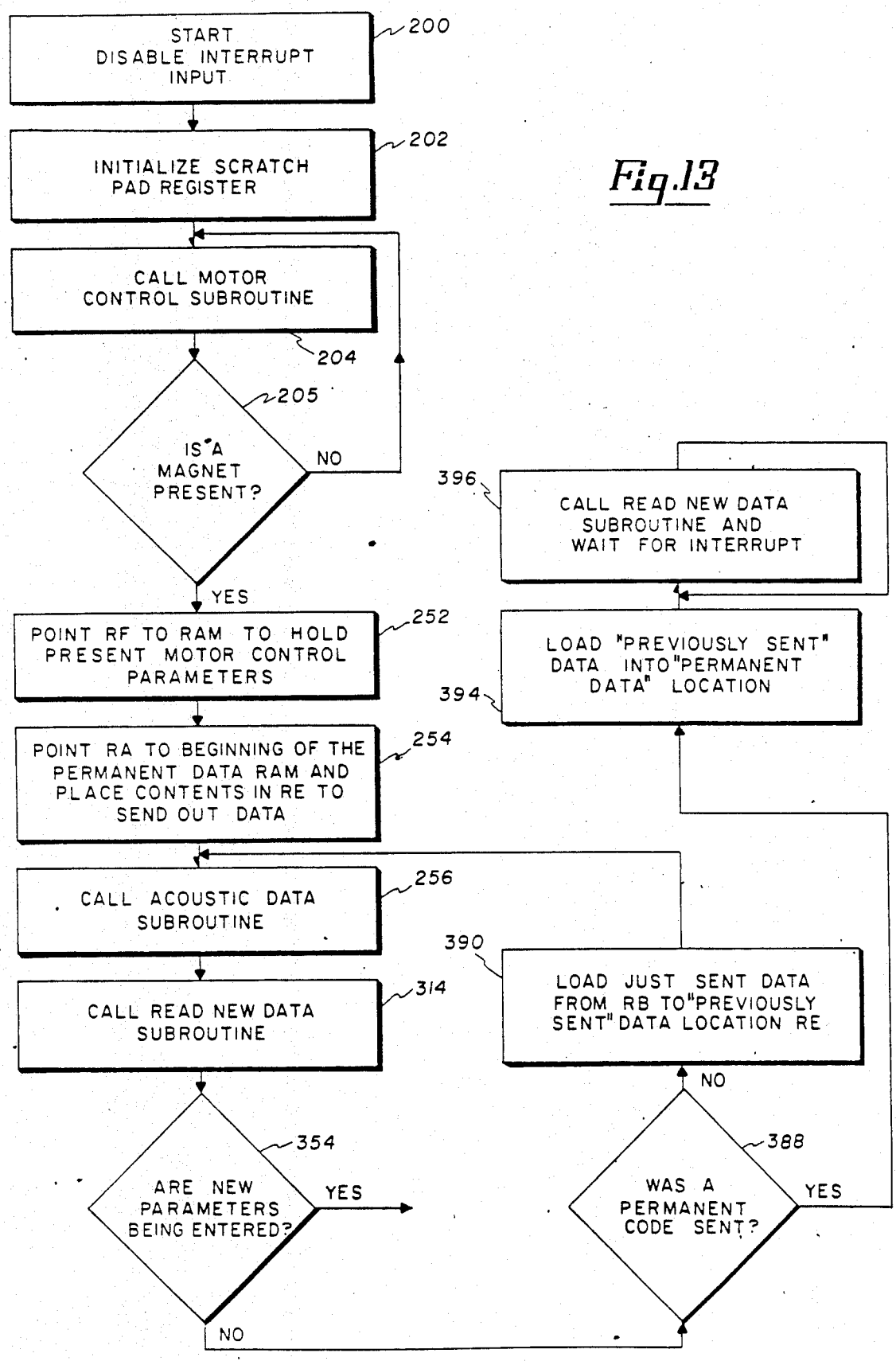
FIG. 13 is a flow chart of the Executive Program.

In FIG. 13, the flow chart of the executive program and in FIGS. 14 through 19, the flow charts of the various subroutines representing the instructions listed above, the corresponding step for each instruction is identified under the heading "Step Location".

The program begins at start step 200 by disabling the interrupt input of the microprocessor 100. The program then transfers to step 202 wherein the various counters are initialized, and the dosage and interval commands are set to a one, one state. The executive program is then called.

Motor Control Subroutine

Figure 14A:
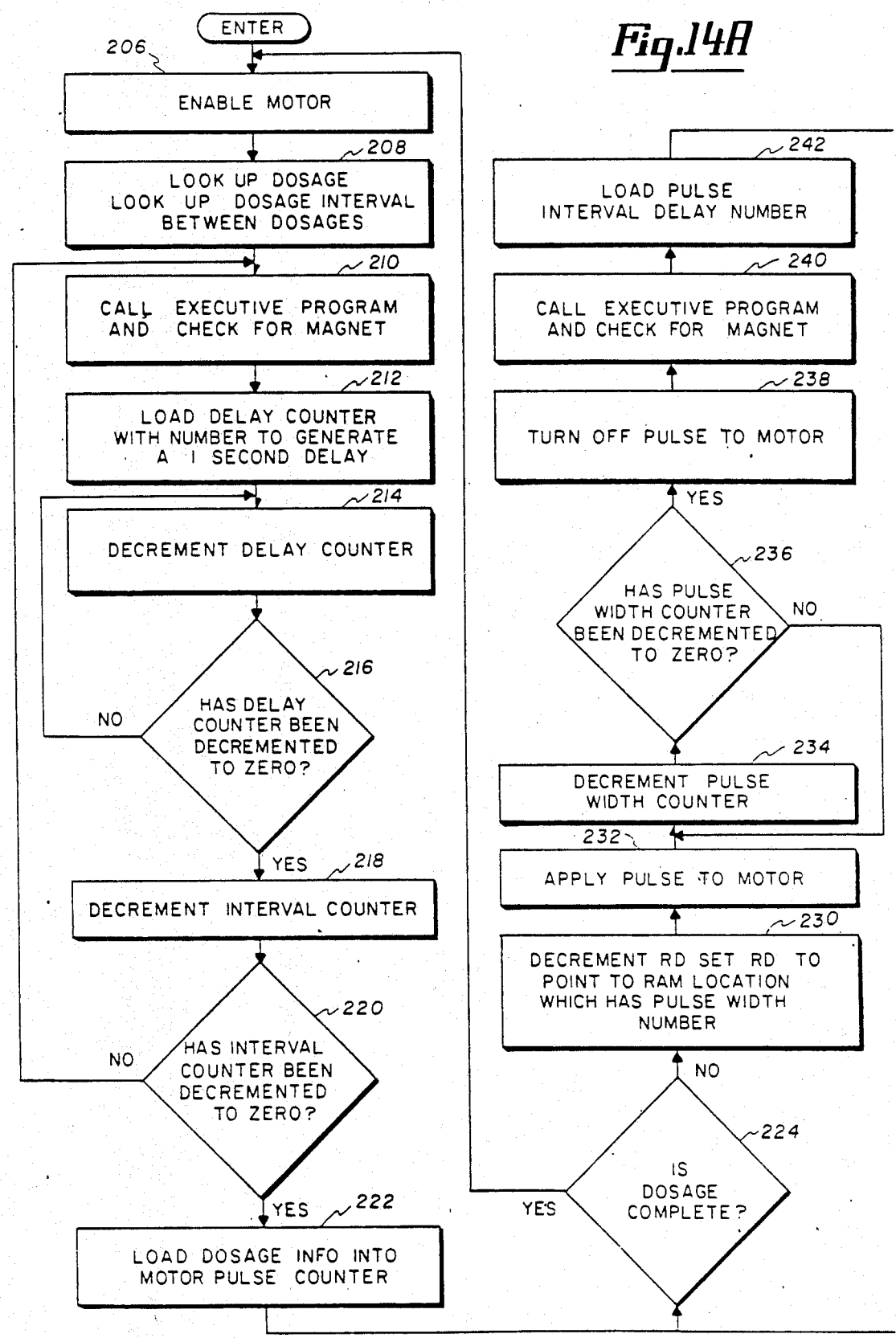
FIG. 14 is a flow chart of the Motor Control Subroutine.
Figure 14B:
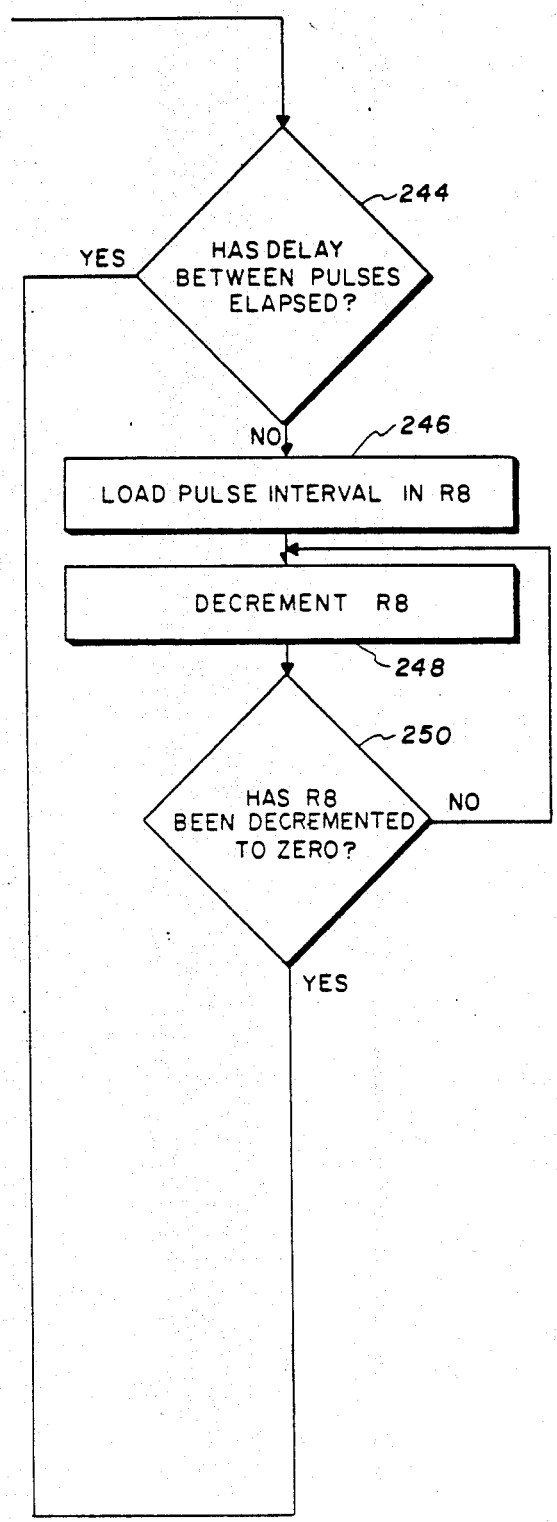

As shown in FIG. 14, the first step in the executive program following the initialization step 202 is the call Motor Control Subroutine step 204. The Motor Control Subroutine as shown in FIG. 14 begins with step 206, where the output port of the microprocessor 100 is set to energize the circuit for driving the stepper motor winding by placing an N0 signal at pin 19 which inhibits the acoustic transducer operation and enables the Q output of microprocessor 100 to toggle the stepper motor winding. The function of the flip-flop A4 is to provide a bipolar pulse to the stepper motor winding connected across pins 10 and 11 of module A6. For every Q output of the processor on pin A1-4, flipflop A4 toggles and steers the current in the stepper motor winding in first one direction and then the other. The pulse width of the waveform at Q determines the width of the motor drive pulses. The stepper motor drivers A8 are connected in parallel to provide sufficient current drive capability to energize the stepper motor winding.

After the motor output is enabled at step 206, at step 208, the working data pointer RF is pointed to the beginning of the interval table, and the working data temporary storage counter RO is pointed to the pulse width and pulse interval table in the RAM. The permanent data pointer RA is pointed to the interval number in the RAM 102B and the number stored in RAM at that location is removed and multiplied by two. The next step which occurs in operation 208 is the pointing of the permanent data temporary pointer to the dosage number in RAM 102B, which is followed by incrementing of the interval table pointer $R_F$ by the number generated from the interval number in RAM. Finally, the interval delay is taken from RAM and loaded into the delay subroutine, shown in FIG. 9 below.

In step 210, the program moves from the motor control subroutine of FIG. 14 back to the executive program at step 205 to check for the magnet. If the magnet is not present, step 205 returns the program back to step 212 in the motor control subroutine. Step 212 involves the loading of the one second delay counter R8 with the basic delay number which will generate a one second delay when decremented from the counter at the normal operating rate of the microprocessor 100 when driven by a 32.768K Hertz crystal. In step 214, the one second counter is decremented by one unit and in step 216, the contents of R8 are tested to see if the counter had been decremented to zero to signify the end of the one second interval.

Steps 214 and 216 are repeated in a loop until the one second delay is completed at which time the program moves to step 218 where the interval counter is decremented and the counter is tested, and if the contents are non-zero, the program branches back to step 210 until the completion of the interval delay called for by the number originally stored in Memory which was transferred to RD at step 208 at the beginning of the motor control subroutine. After completion of the indicated interval delay, the subroutine moves to step 222.

In step 222, the working data pointer $R_F$ is pointed to the dosage table in RAM 102B and the dosage data which is two bytes in length is then loaded into RD. That number represents the number of motor pulses to be delivered to apply the dosage called for by the stored command received from the external programmer.

Next, step 224 makes an initial check to determine whether the dosage counter is set at zero to indicate that the external programmer was set to call for a zero level dosage. If it is zero, the subroutine branches back to the beginning of Motor Control Subroutine, continuing to run intervals without delivering any pulses to the motor. If the dosage counter is not loaded with a zero, the subroutine moves to step 230 which decrements RD, and gets pulse width number from RAM pointed to by RO, and increments RO to point at the pulse interval number. In step 232, the drive of the motor commences by setting the Q output of microprocessor 100 to a one state to toggle flip-flop A4 to pulse the stepper motor winding to drive the roller pump and dispense a measured dosage of drug to the body through catheter 22. For every Q output of the microprocessor 100 on pin A1-4, flip-flop A4 toggles and steers the current in the stepper motor winding in first one direction and then the other. The duration of the Q output as a logic one is determined by the number pointed to by R0.

The motor continues to be driven by pulses as the accumulator D is decremented in step 234 and its contents tested in step 236. After the pulse width counter has counted down to zero, the subroutine moves to step 238 to change the Q output of the microprocessor 100 to logic zero to terminate the pulse to the motor. The subroutine progresses to step 240 by calling the executive program to again check for the presence of a magnet in the same fashion that the check is made once each interval unit at step 210. If no magnet is present, control is returned to the motor control subroutine, which moves to step 242.

At step 242, the pulse interval delay number is loaded into R8 and R0 is pointed back to the pulse width delay number stored in RAM 102. The pulse interval delay number is checked at step 244. If the delay is equal to zero, the program moves immediately back to step 224, and the motor delivers the prescribed number of pulses for the dosage.

If the test at 244 indicates that a nonzero pulse interval delay is called for, that delay is loaded at step 246 into the delay counter R8, decremented at step 248, and that counter's output is tested at step 250 until the counter is fully decremented to zero and the motor control returns to step 224, where it again checks to see if dosage is complete.

Acoustic Output Subroutine and One Second Delay Subroutine

Figure 15A:
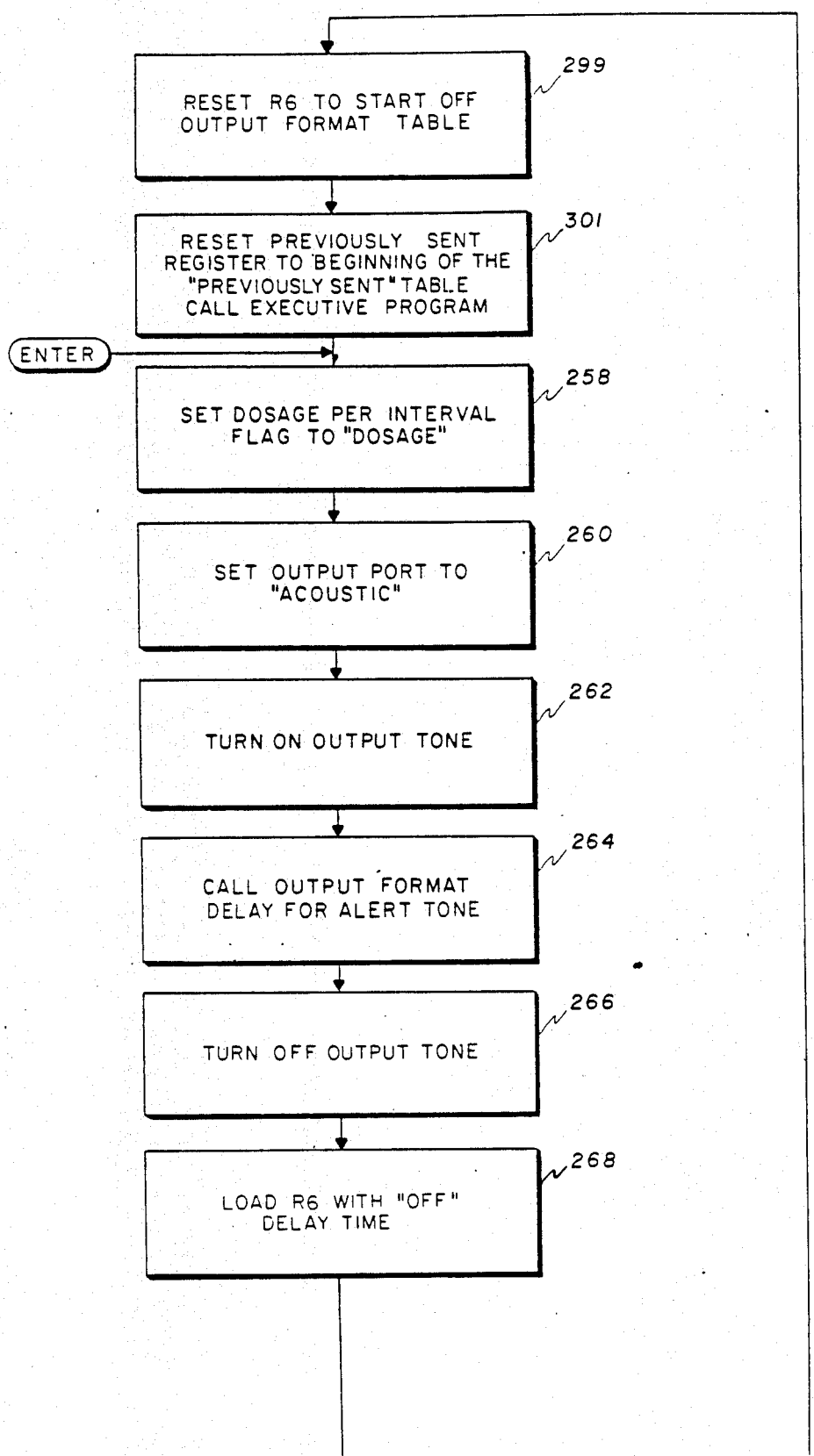
FIG. 15 is a flow chart of the Acoustic Output Data Subroutine.
Figure 15B:
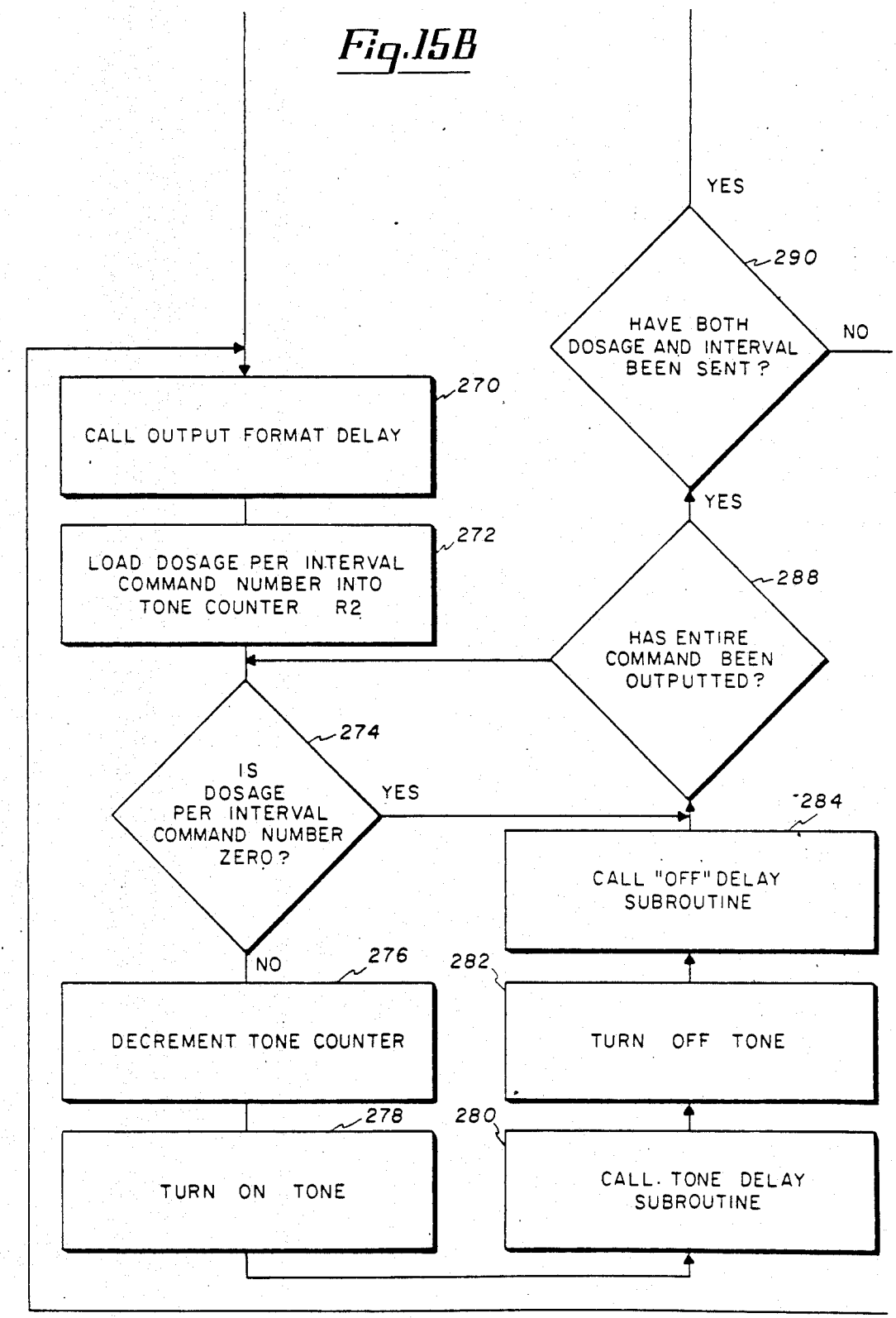

If a magnet is detected after one of the one second intervals that are set up by the motor control subroutine or in the period immediately following completion of application of a pulse to the stepper motor, the reed switch is closed and the signal at pin A1-24 of microprocessor 100 switches from a logic HIGH to a LO on EF1 and the processor program reverts to an acoustic program output subsystem mode as shown in FIG. 15. The output subroutine is called after the test at step 205 of the executive program detects the presence of a magnet, and the executive program moves to step 252. At step 252, the working data pointer is pointed to the RAM 102 to store the present motor control parameters. At step 254, the permanent data memory pointer is pointed to the beginning of the permanent data RAM, and the contents of that memory location are placed in the previously sent data memory pointer for transmission by the acoustic output subroutine. At 256, the acoustic data subroutine of FIG. 15 is called.

Acoustic Output and Output Delay Subroutines.

Referring now to the acoustic output subroutine of FIG. 15 at step 258, the dosage interval flag R7 is set to "dosage". At step 260, the output port is set via the N1 output strobe. The gates having outputs A5-3 and A5-4 perform an "anding" function with the Q signal of the microprocessor and pin 13 of flip-flop A7. Flip-flop A7, at pin 13, is enabled by an N1 output of the processor at pin A1-18 to allow the timing pulse signal TPA at pin A1-34 to toggle flip-flop A7-13 and provide a 50 percent duty cycle 2 KHZ signal at pin A5-1. The microprocessor Q output at pin A1-4 modulates the 2 KHz audio tone by the input to A5-2. When the acoustic transducer is selected by an N1 output, the toggling of the stepper motor via flip-flop A4 is inhibited.

At step 262, the output tone is enabled by driving the Q output of microprocessor 100 at pin 4. At step 264, the output format delay subroutine of FIG. 9 is called for the generation of the time delay for the alert tone. After the time delay, the subroutine steps to 266 and the tone is terminated by setting Q to logic zero.

The one second, or output delay subroutine shown in FIG. 16 operates as follows. The subroutine commences with step 300 which calls for loading of the acoustic delay number from the output format table pointed to by R6. At step 302 the unit time number is loaded into R8, the one second delay counter. In the illustrative embodiment shown, the time interval selected is one second, so that the various tones and time delays are all multiples of one second. In step 304, the counter R8 is decremented and tested at step 306 repetitively until completion of the time delay when the program moves to step 308, which calls for decrementing RD to make sure that the selected number of delay times has occurred. If the number of seconds which have elapsed is less than the number called for by RD, the subroutine loops back to step 302. Once the appropriate number of delay time intervals has occurred and RD is fully decremented, the subroutine branches back to step 312, and exits back to the next step in the output subroutine shown in FIG. 15.

Resuming discussion of the output subroutine of FIG. 15, the next step following the turn off of the alert tone at step 266 is the setting of R6, with the delay time between the alert tone and the commencement of the tones representing the output data. In the embodiment shown, this is a one second delay.

Figure 16:
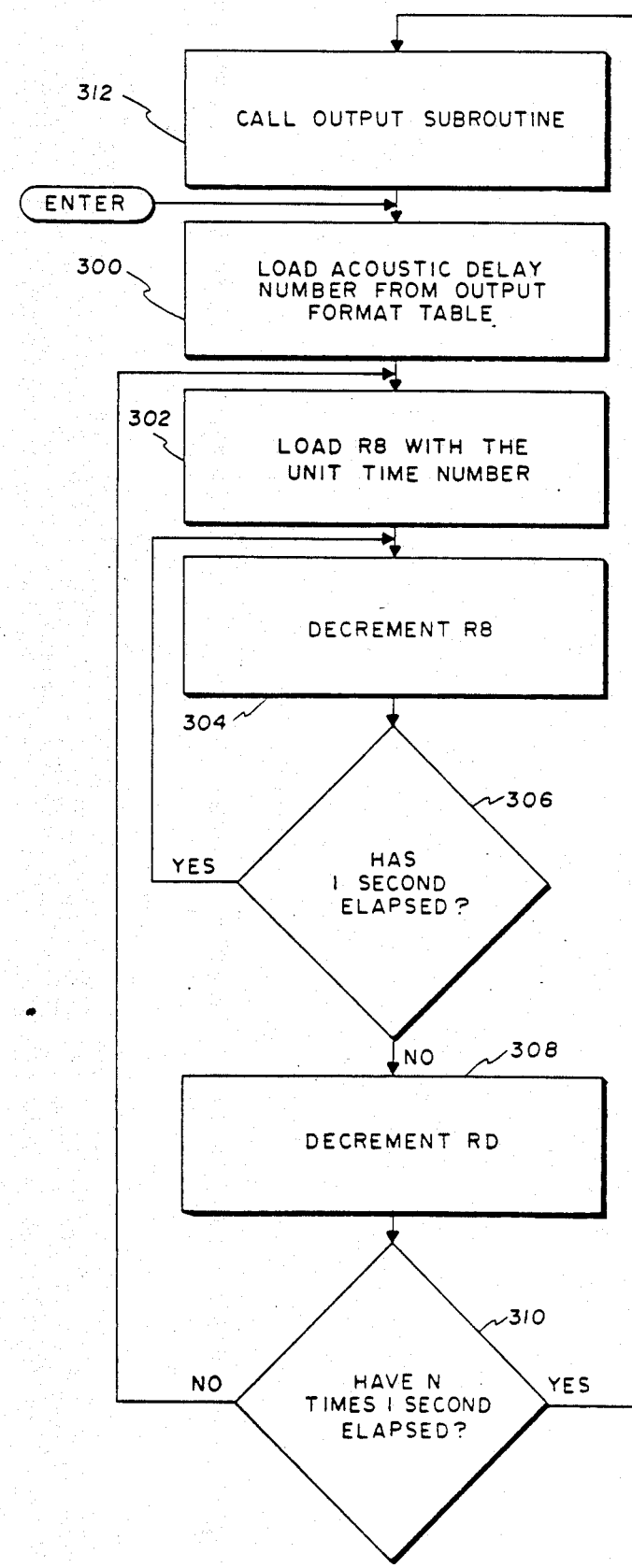
FIG. 16 is a flow chart of the Output Delay Subroutine.

The next step 270 is another one second delay generated by the one second delay subroutine of FIG. 16. Step 272 causes loading of the dosage number into the tone counter R2. The contents of the tone counter are then tested at step 274 and if equal to zero, causes the program to branch forward to step 288. If the tone counter is set with a non-zero number, the next step is to decrement the tone counter at step 276, turn on the tone at step 278, to have the tone's duration determined by the tone delay subroutine of FIG. 16 at step 280, and turn off the tone at 282 after the time interval elapses. Following step 282, the time delay subroutine is again called at step 284 to generate the interval that the tone is turned off and the next step, 288, is to determine whether all data has been sent. If all data had not then sent, the subroutine branches back to step 274, and repeats. Thus, the data transmitted is the five second alert tone, the one second space, and a number of one second tones separated by one second spaces to represent the command increments.

After the dosage information is transmitted, the subroutine moves from step 288 to step 290, and the dosage interval flag is checked. If the flag is still set at dosage, the test at 290 results in a NO answer indicating that both the dosage and interval information have not yet been sent. In step 294, the dosage/interval flag is reset to interval by decrementing R7. The subroutine then moves to step 296, which creates a two second delay by using the output format table and one second delay subroutine. In step 298, the tone delay subroutine of FIG. 9 is called to create another one second delay. Thus, after delivery of the dosage information tones, there is a three second delay and the subroutine moves back to step 270, where the same steps are repeated to deliver the interval data as a series of tones each of which are separated by one second. After completion of the delivery of the interval information, the checking of the dosage/interval flag results in a yes answer to the test at step 290, and the program advances to step 300, where R6 is set to the start of the output format table in preparation for the next time that the acoustic output subroutine is entered. In the embodiment shown, the format table pointer is reset at step 299 to call for a five second format delay. The next step 301 resets the previously sent register to the beginning of the previously sent table, and calls the executive program.

Read New Data Subroutine.

Figure 17A:
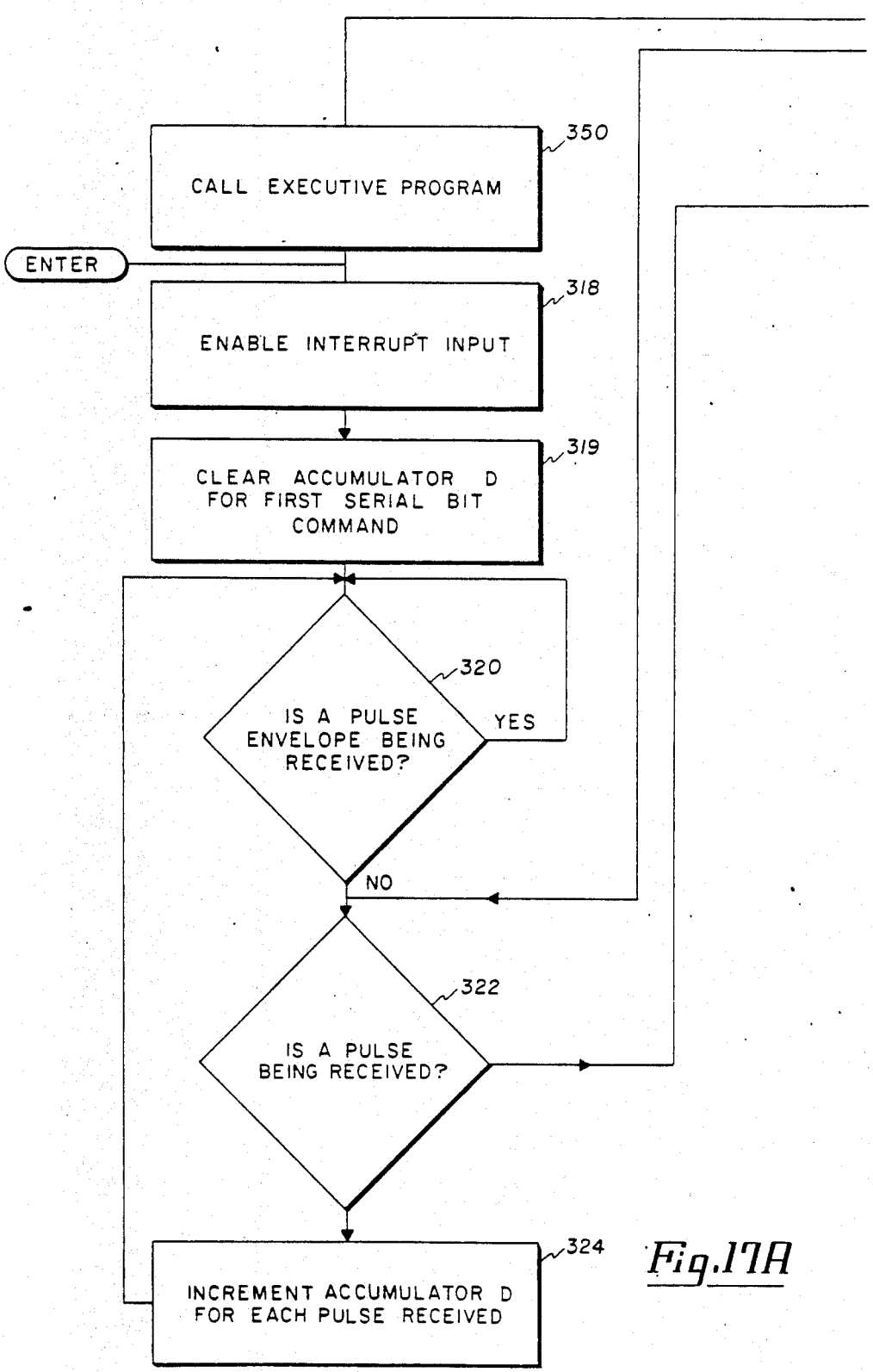
FIG. 17 is a flow chart of the Read New Data Subroutine.
Figure 17B:
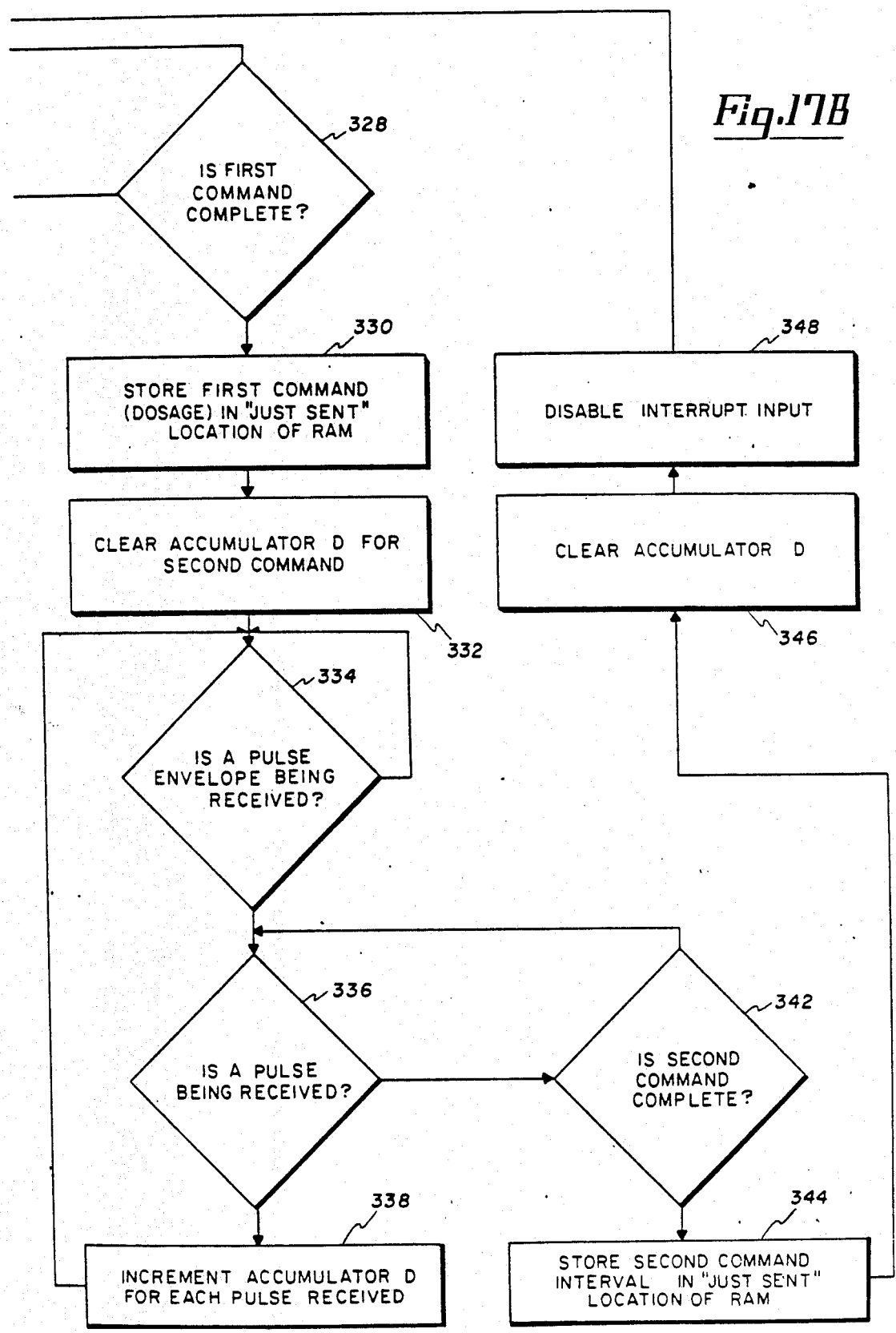

The next step reached in the executive program is step 314, which is the call for the read new data subroutine of FIG. 17. Referring now to FIG. 17, the first step in the read new data subroutine is step 318, which enables the interrupt input. The next step of the read new data subroutine is step 319, to clear accumulator D, which will be used to count and temporarily store the pulses which indicate dosage/interval commands. As the first pulses are being received, the program at 320, 322, and 328 tests the flags $\overline{EF3}$ and $\overline{EF2}$ whose states are dependent upon receipt of the radio frequency pulses from the external programmer. $\overline{EF2}$ is the microprocessor input which indicates individual pulses. $\overline{EF3}$ is the microprocessor input which indicates the envelope of a burst of multiple pulses. In other words, the processor at step 328, examines the $\overline{EF3}$ input to determine whether the first group of pulses representing dosage have been completed and whether a second group of pulses representing interval is coming. After the first group of pulses have been completely received, the subroutine progresses to step 330, where the first or dosage command is stored in the RAM in the JUST SENT location.

The counter accumulator D is then cleared to receive the second transmitted command. The tests of $\overline{EF2}$ and $\overline{EF3}$ are performed by program steps 334 and 336 and 342, and each received pulse is used to increment the accumulator D counter by one count at step 338. After completion of the pulse envelope and cessation of $\overline{EF3}$, the subroutine progresses to step 344, and the content of the accumulator D is stored in RAM in the JUST SENT location. The subroutine then clears the accumulator D at step 346 and disables the interrupt input at step 348 and recalls the executive program at step 350.

Accept New Motor Parameters Subroutine

After completion of the read new data subroutine, the executive program counter advances the program to step 354, where the test is made to see if the appropriate code for accepting new parameters has been received. That test is performed at step 354. The code indicating that new motor parameters are to be received is the receipt of a code of nine and X. If that code is received, the branch from step 354 is to the Accept New Motor and Dosage Parameters Subroutine of FIG. 18.

Referring now to FIG. 18, the first step 356 in the Accept New Data subroutine is to load zero into the location just prior to the first entry of the dosage table in the RAM. At step 358, R0 points to the pulse interval RAM location. At step 360, a zero is loaded into the JUST SENT RAM location to check for data received later. At step 362, the READ NEW DATA subroutine of FIG. 10 is called to obtain the first byte of data which is representative of the pulse interval. In receiving this data for loading into the RAM, the READ NEW DATA subroutine operates in precisely the same manner that it operated in receiving the interval and dosage commands.

In step 364, the two numbers received from the READ NEW DATA subroutine are between 01 and 10 (HEX). A one is then subtracted from the numbers to obtain a number between 0 and F (HEX), and then stored in register E while a one is subtracted from the second number for the same reason. The two numbers are assembled together and stored in the memory at the location pointed to by R0 as a number between 00 and FF (HEX) as the first parameter. R0 is then decremented to accept a second parameter in the same manner as described above. The complete dosage table is loaded one byte at a time as above until the table is filled with seven two byte numbers. The program then goes back to the initialization of registers in the Executive Program subsequent to step 202. This restarts the entire program and sends out a code of 1,1 from the Acoustic Output Subroutine, so that the system with its new parameter data is then ready to accept the programming of the interval and dosage commands in the normal fashion.

After the new parameter information is received and the executive program has stepped through the read new data subroutine, and advanced to step 354 and received an indication that no new parameters are to be received, the program steps to step 388 of FIG. 13, and determines if the make permanent code has been received, the new data is transferred from the JUST SENT to the PREVIOUSLY SENT data RAM locations at step 390. If the make permanent code has not been received, the test of step 392 advances the executive program to step 398 where the Just Sent Data from RAM is moved to the previously sent data locations, and the acoustic data subroutine is called at step 256. The process of continually reading new data through the Read New Data subroutine and outputting that new data through the acoustic data subroutine continues until a make permanent code is received and the test at step 388 is a yes. The program than steps to step 394, which causes the Previously Sent Data to be loaded into the Permanent Data locations. The program then steps into the Read New Data Subroutine at step 396, and continues to operate in the Read New Data Subroutine until the interrupt signal is received by removing the magnet and opening the reed switch.

Interrupt Subroutine

Figure 19:
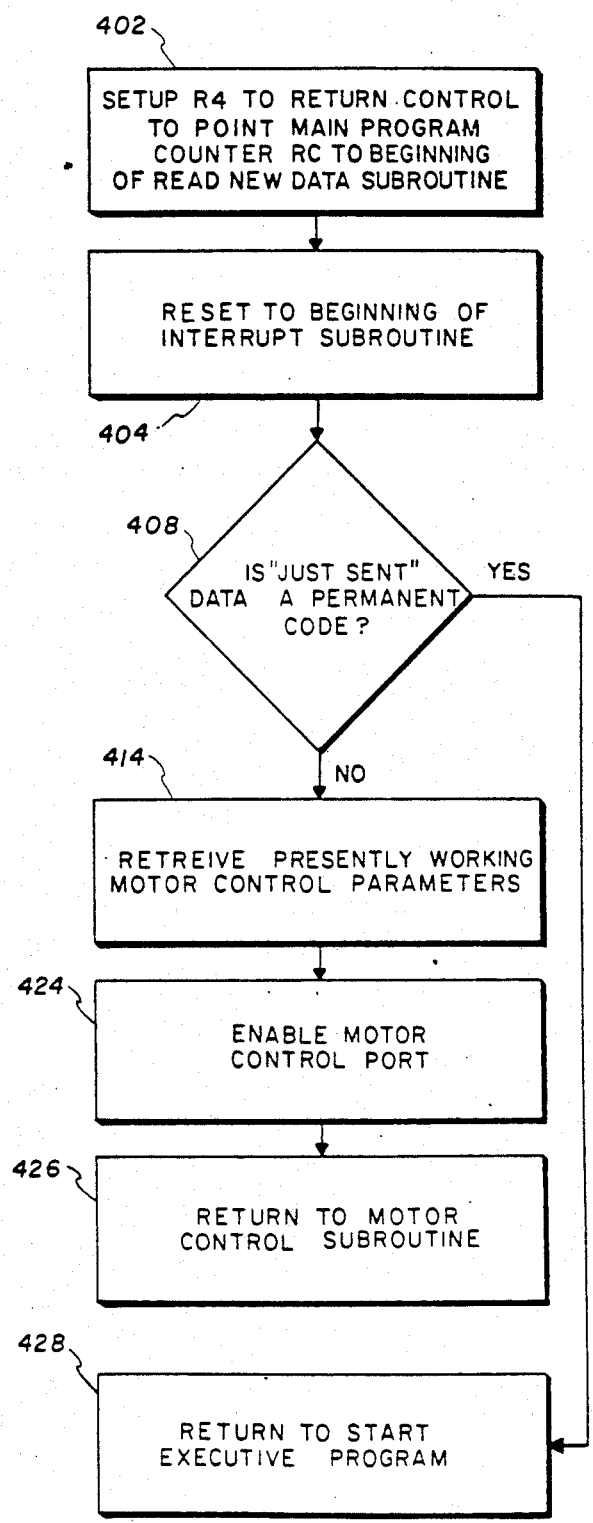
FIG. 19 is a flow chart of the Interrupt Subroutine.

The Interrupt Subroutine is shown in FIG. 19. The Interrupt Subroutine is entered from the Accept New Data Subroutine. The Interrupt Subroutine is initiated when the reed switch opens as the magnet is removed to remove the LOGIC 1 from the $\overline{INT}$ input at pin A1-36 of the microprocessor 100 when the interrupt input has been enabled by the program.

At step 402, the main program counter R4 is set up to return control to the main program counter and RC, the read new data counter, is set up to the beginning of the Read New Data Subroutine. At step 404, the Interrupt Subroutine is restored. Step 408 is a check to see if the Just Sent Data in the location of memory pointed to by RB is a permanent code. If the just sent data is a permanent code, the program is restarted by moving to step 428. At step 428, we go back to the start of the Executive Program.

If, at step 408, it is determined that the just sent data was not a permanent code, the program moves through steps 414 through 426 back to the executive program. In that situation at step 416, the working data pointer is pointed at the RAM to retrieve the presently working motor control perameters, and at 424, the motor control port is selected and the motor control subroutine is enabled at 426.

I claim:

1. A medical device comprising:
   reservoir for the storage of liquid;
   means operatively coupled to said reservoir for dispensing said liquid;
   means operatively coupled to said dispensing means for controlling said dispensing means in response to programming signals; and
   means for generating programming signals wherein said programming signals further comprise a set of dispensing signals wherein each of said dispensing signals further comprises a dosage value and an interval value representing a time period wherein no liquid is dispensed.

2. A medical device according to claim 1 wherein said controlling means further comprises a microprocessor having memory means for storing each of said set of dispensing signals and timing means for sequentially causing said dispensing means to dispense from said reservoir an amount of said liquid corresponding to said dosage value after the elapse of said interval value for each of said dispensing signals within said set of dispensing signals.

3. A medical device according to claim 2 wherein said generating means causes an interrupt to said microprocessor upon generation of said programming signals.

4. An implantable medical device comprising:
   reservoir for the storage of a liquid;
   means operatively coupled to said reservoir for dispensing said liquid;
   means for receiving external programming signals comprising updated dosage information and internal command information signals;
   means operatively coupled to said dispensing means for controlling said dispensing means in response to said external programming signals; and
   means operatively coupled to said controlling means for inhibiting said dispensing means while receiving said external programming signals.

5. An implantable medical device according to claim 4 further comprising:
   means operatively coupled to said controlling means for reinitiating said dispensing means upon completion of said external programming signals.

6. An implantable medical device comprising:
   reservoir for the storage of a liquid;
   means operatively coupled to said reservoir for dispensing said liquid;
   means for receiving external programming commands;
   means responsively coupled to said receiving means for storing said external programming commands;
   means operatively coupled to said dispensing means for controlling said dispensing means in response to said stored external programming commands; and
   means for notifying an operator of said external programming commands stored in said storing means.

7. An implantable medical device according to claim 6 further comprising:
   means for powering either said dispensing means or said notifying means.

8. A drug dispenser system comprising:
   external programmer means for generating and transmitting programming signals, said programming signals comprising time interval data, dosage data and metering control data and means for individually generating and transmitting said programming signals;
   an implantable drug dispenser which includes:
   reservoir means for storage of a liquid drug;
   delivery means for delivering said liquid drug to the human body;
   metering means, coupled between said reservoir means and said delivery means for controlling the flow of drug from said reservoir means to said human body;
   receiver means for receiving said time interval data, dosage data and metering control data, said receiver means further comprising first storage means for storing said time interval data, second storage means for storing said dosage data, and third storage means for storing said metering control data, said third storage means having a plurality of individually addressable storage locations, said dosage data indicative of one of said plurality of said individually addressable storage locations of said third storage means;
   timer means responsive to said dosage interval data stored in said first storage means for timing out a dosage interval and for initiating a dosage interval time out signal at the expiration of said dosage interval; and
   control means responsive to said timing means for causing said metering means to deliver a predetermined quantity of said liquid drug in response to said dosage interval time out signal, said control means comprising addressing means coupled to said second storage means and said third storage means for addressing said third storage means at said one of said plurality of storage locations of said third storage means indicated by said dosage data in said second storage means and metering control means for controlling operation of said metering means according to said metering control data in said addressed one of said plurality of storage locations in said third storage means.

9. A system according to claim 8 wherein said metering means comprises a roller pump coupled thereto a stepper motor coupled thereto wherein said pump is driven by said stepper motor, and wherein said metering control data specifies a predetermined operational sequence for said stepper motor.

10. A system according to claim 9 wherein said metering control comprises means for generating a predetermined number of electrical pulses in combination with said stepper motor wherein said pulses are applied to said stepper motor, and wherein said metering control means applies said predetermined number of electrical pulses to said stepper motor.

11. A system according to claim 10 wherein said metering control data further comprises data indicative of pulse widths of and pulse intervals between said predetermined number of electrical pulses to be applied to said stepper motor, wherein said receiver means further comprises fourth storage means for storing said metering data related to pulse intervals and pulse widths, and wherein said metering control means applies said predetermined number of electrical pulses to said stepper motor in accordance with said metering control data stored in said fourth storage means.

* * * * *

UNITED STATES PATENT AND TRADEMARK OFFICE
CERTIFICATE OF CORRECTION

PATENT NO. : 4,692,147
DATED : Sep. 8, 1987
INVENTOR(S) : Stephen R. Duggan

It is certified that error appears in the above-identified patent and that said Letters Patent are hereby corrected as shown below:

Column 2, line 25, "datailed" should be --detailed--;

Column 11, line 5, "IO" should be --TO--;

Column 11, line 54, "PLC" should be "PLO"; and

Claim 9, line 2, "coupled thereto" should be deleted and replaced by a comma.

Signed and Sealed this

Twentieth Day of December, 1988

Attest:

DONALD J. QUIGG

Attesting Officer      Commissioner of Patents and Trademarks